US008609629B2

(12) United States Patent
Giordano et al.

(10) Patent No.: US 8,609,629 B2
(45) Date of Patent: **\*Dec. 17, 2013**

(54) KITS AND METHODS FOR NUTRITION SUPPLEMENTATION

(75) Inventors: John A. Giordano, West Orange, NJ (US); Charles J. Balzer, West Orange, NJ (US)

(73) Assignee: Evertt Laboratories, Inc., Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/356,247

(22) Filed: Jan. 23, 2012

(65) Prior Publication Data

US 2012/0121726 A1    May 17, 2012

Related U.S. Application Data

(63) Continuation of application No. 12/422,091, filed on Apr. 10, 2009, now Pat. No. 8,101,587, which is a continuation-in-part of application No. 11/928,610, filed on Oct. 30, 2007, now Pat. No. 8,197,855, which is a continuation of application No. 10/916,534, filed on Aug. 12, 2004, now Pat. No. 7,560,123.

(51) Int. Cl.
| A61K 31/70 | (2006.01) |
| A61K 31/525 | (2006.01) |
| A61K 31/51 | (2006.01) |
| A61K 31/355 | (2006.01) |
| A61K 31/34 | (2006.01) |
| A61K 31/07 | (2006.01) |

(52) U.S. Cl.
USPC ............. 514/52; 514/168; 514/251; 514/276; 514/458; 514/474; 514/558; 514/559; 514/725; 514/904; 514/943

(58) Field of Classification Search
USPC ........... 514/52, 168, 251, 276, 458, 474, 558, 514/559, 725, 904, 943
See application file for complete search history.

(56) References Cited

U.S. PATENT DOCUMENTS

| 3,160,564 A | 12/1964 | Hanus |
| 3,608,083 A | 9/1971 | Bunnell |
| 3,846,550 A | 11/1974 | Aakrongold |
| 4,124,710 A | 11/1978 | Descamps |
| 4,251,550 A | 2/1981 | Proctor |
| 4,374,082 A | 2/1983 | Hochschild |
| 4,431,634 A | 2/1984 | Ellenbogen |
| 4,547,488 A | 10/1985 | Merkel |
| 4,619,829 A | 10/1986 | Motschan |
| 4,710,387 A | 12/1987 | Uiterwaal et al. |
| 4,740,373 A | 4/1988 | Kesselman et al. |
| 4,752,479 A | 6/1988 | Briggs et al. |
| 4,804,535 A | 2/1989 | Kesselman et al. |
| 4,814,102 A | 3/1989 | Baur et al. |
| 4,863,898 A | 9/1989 | Ashmead et al. |
| 4,940,658 A | 7/1990 | Allen et al. |
| 4,945,083 A | 7/1990 | Jansen |
| 4,994,283 A | 2/1991 | Mehansho et al. |
| 5,108,767 A | 4/1992 | Mulchandani et al. |
| 5,215,750 A | 6/1993 | Keane |
| 5,215,754 A | 6/1993 | Valorose |
| 5,278,329 A | 1/1994 | Anderson |
| 5,340,315 A | 8/1994 | Kaye |
| 5,340,594 A | 8/1994 | Barclay |
| 5,374,560 A | 12/1994 | Allen et al. |
| 5,407,957 A | 4/1995 | Kyle et al. |
| 5,438,017 A | 8/1995 | Allen |
| 5,457,055 A | 10/1995 | Allen et al. |
| 5,492,938 A | 2/1996 | Kyle et al. |
| 5,494,678 A | 2/1996 | Paradissis et al. |
| 5,514,382 A | 5/1996 | Sultenfuss |
| 5,556,644 A | 9/1996 | Chandra |
| 5,563,126 A | 10/1996 | Allen et al. |
| 5,569,458 A | 10/1996 | Greenberg |
| 5,626,884 A | 5/1997 | Lockett |

(Continued)

FOREIGN PATENT DOCUMENTS

| EP | 0482715 | 4/1992 |
| EP | 0891719 | 1/1999 |

(Continued)

OTHER PUBLICATIONS

Everett Laboratories, Inc.'s Complaint against River's Edge Pharmaceuticals, LLC, filed Jul. 14, 2009.
Everett Laboratories, Inc.'s Notice of Motion for Preliminary Injunction as to Trademark Claims, filed Jul. 31, 2009.
Everett Laboratories, Inc.'s Notice of Motion for Preliminary Injunction as to Patent Claims, filed Jul. 31, 2009.
Defendant's Brief in Opposition to Plaintiffs Motion for Preliminary Injunction, filed Aug. 25, 2009.
Plaintiffs Reply Brief in Support to Plaintiffs Motion for Preliminary Injunction as to Patent claims, filed Sep. 2, 2009.
Plaintiffs Reply Brief in Support to Plaintiffs Motion for Preliminary Injunction as to Trademark Claims, filed Sep. 2, 2009.

(Continued)

*Primary Examiner* — Kevin E Weddington
(74) *Attorney, Agent, or Firm* — Don J. Pelto, Esquire; Sheppard, Mullin, Richter & Hampton LLP

(57) ABSTRACT

The present invention relates to methods of co-administration of various vitamin and mineral compositions, and in a specific embodiment, said methods comprise co-administering one composition comprising vitamin A, beta carotene, B-complex vitamins, vitamin C, vitamin $D_3$, vitamin E, iron, magnesium and zinc, and a second composition comprising omega-3 fatty acids such as DHA, to supplement the nutritional needs of individuals within physiologically stressful states; and kits provided for co-administration of various vitamin and mineral compositions, and in a specific embodiment, said kits comprise one composition comprising vitamin A, beta carotene, B-complex vitamins, vitamin C, vitamin $D_3$, vitamin E, iron, magnesium and zinc, and a second composition comprising omega-3 fatty acids such as DHA, to supplement the nutritional needs of individuals within physiologically stressful states.

54 Claims, No Drawings

(56) References Cited

U.S. PATENT DOCUMENTS

| | | | |
|---|---|---|---|
| 5,686,429 | A | 11/1997 | Lin et al. |
| 5,770,215 | A | 6/1998 | Moshyedi |
| 5,780,451 | A | 7/1998 | DeMichele et al. |
| 5,795,873 | A | 8/1998 | Allen |
| 5,869,084 | A | 2/1999 | Paradissis et al. |
| 5,898,036 | A | 4/1999 | McLeod |
| 5,914,129 | A | 6/1999 | Mauskop |
| 5,922,704 | A | 7/1999 | Bland |
| RE36,288 | E | 8/1999 | Lin et al. |
| 5,932,624 | A | 8/1999 | Herbert |
| 5,948,443 | A | 9/1999 | Riley |
| 5,965,162 | A | 10/1999 | Fuisz et al. |
| 5,976,568 | A | 11/1999 | Riley |
| 5,997,915 | A | 12/1999 | Bailey |
| 6,039,978 | A | 3/2000 | Bangs et al. |
| 6,042,849 | A | 3/2000 | Richardson |
| 6,048,846 | A | 4/2000 | Cochran |
| 6,054,128 | A | 4/2000 | Wakat |
| 6,090,414 | A | 7/2000 | Passwater |
| 6,093,425 | A | 7/2000 | Kamarei |
| 6,102,706 | A | 8/2000 | Khoo et al. |
| 6,103,756 | A | 8/2000 | Gorsek |
| 6,136,345 | A | 10/2000 | Grimmett |
| 6,136,859 | A | 10/2000 | Henriksen |
| 6,139,872 | A | 10/2000 | Walsh |
| 6,207,651 | B1 | 3/2001 | Allen |
| 6,214,373 | B1 | 4/2001 | Snowden |
| 6,218,192 | B1 | 4/2001 | Altura et al. |
| 6,228,388 | B1 | 5/2001 | Paradissis et al. |
| 6,245,360 | B1 | 6/2001 | Markowitz |
| 6,255,341 | B1 | 7/2001 | DeMichele et al. |
| 6,258,846 | B1 | 7/2001 | Hermelin et al. |
| 6,297,224 | B1 | 10/2001 | Allen et al. |
| 6,299,896 | B1 | 10/2001 | Cooper et al. |
| 6,352,713 | B1 | 3/2002 | Kirschner et al. |
| 6,361,800 | B1 | 3/2002 | Cooper et al. |
| 6,410,281 | B1 | 6/2002 | Barclay |
| 6,436,431 | B1 | 8/2002 | Hoffpauer et al. |
| 6,440,450 | B1 | 8/2002 | Han |
| 6,444,218 | B2 | 9/2002 | Han |
| 6,447,809 | B1 | 9/2002 | Krumhar et al. |
| 6,451,341 | B1 | 9/2002 | Slaga et al. |
| 6,451,567 | B1 | 9/2002 | Barclay |
| 6,488,956 | B1 | 12/2002 | Paradissis et al. |
| 6,495,177 | B1 | 12/2002 | deVries et al. |
| 6,500,472 | B2 | 12/2002 | Uchida et al. |
| 6,521,247 | B1 | 2/2003 | deVries |
| 6,528,496 | B1 | 3/2003 | Allen et al. |
| 6,569,445 | B2 | 5/2003 | Manning et al. |
| 6,572,888 | B2 | 6/2003 | Byrd |
| 6,576,253 | B2 | 6/2003 | Manning et al. |
| 6,579,544 | B1 | 6/2003 | Rosenberg |
| 6,607,900 | B2 | 8/2003 | Bailey et al. |
| 6,660,293 | B2 | 12/2003 | Giordano et al. |
| 6,814,983 | B2 * | 11/2004 | Giordano et al. ............ 424/630 |
| 6,818,228 | B1 | 11/2004 | Walsdorf et al. |
| 6,849,613 | B2 | 2/2005 | Prasad |
| 6,866,873 | B2 | 3/2005 | Stern |
| 6,914,073 | B2 | 7/2005 | Boulos et al. |
| 6,977,167 | B2 | 12/2005 | Barclay |
| 7,390,509 | B2 | 6/2008 | Giordano et al. |
| 7,422,758 | B2 | 9/2008 | Block et al. |
| 7,560,123 | B2 * | 7/2009 | Giordano et al. ............ 424/614 |
| 7,704,542 | B2 | 4/2010 | Bydlon et al. |
| 8,101,586 | B2 * | 1/2012 | Rock et al. .................. 514/44 R |
| 8,197,855 | B2 * | 6/2012 | Giordano et al. ............ 424/641 |
| 2001/0028897 | A1 | 10/2001 | Hammerly |
| 2002/0015742 | A1 | 2/2002 | Jackson et al. |
| 2002/0025310 | A1 | 2/2002 | Bland |
| 2002/0034543 | A1 | 3/2002 | Kirschner et al. |
| 2002/0044969 | A1 | 4/2002 | Harden et al. |
| 2002/0187205 | A1 | 12/2002 | Paradissis et al. |
| 2002/0192265 | A1 | 12/2002 | Manning et al. |
| 2003/0049352 | A1 | 3/2003 | Mehansho et al. |
| 2003/0060509 | A1 * | 3/2003 | Elswyk ..................... 514/560 |
| 2003/0068372 | A1 | 4/2003 | Kirschner et al. |
| 2003/0108594 | A1 | 6/2003 | Manning et al. |
| 2003/0206969 | A1 | 11/2003 | Nidamary et al. |
| 2004/0043043 | A1 | 3/2004 | Schkyter et al. |
| 2005/0170479 | A1 | 8/2005 | Weaver et al. |
| 2006/0034916 | A1 | 2/2006 | Giordano et al. |
| 2006/0088574 | A1 | 4/2006 | Manning et al. |
| 2006/0099693 | A1 | 5/2006 | Kobzeff et al. |
| 2006/0153824 | A1 | 7/2006 | Giordano et al. |
| 2006/0165735 | A1 | 7/2006 | Abril et al. |
| 2006/0217385 | A1 | 9/2006 | Edwards et al. |
| 2008/0152725 | A1 | 6/2008 | Giordano et al. |

FOREIGN PATENT DOCUMENTS

| | | |
|---|---|---|
| GB | 822127 | 10/1959 |
| GB | 975387 | 11/1964 |
| JP | 2003012554 | 1/2003 |
| JP | 200359028 | 6/2003 |
| WO | 9907419 | 2/1999 |

OTHER PUBLICATIONS

Physicians Desk Reference, 1999 Edition, Vitafol-PN Caplet Product.
Amine et al., J. Nutrition, 101:927-936 (1971).
Vitafol® product insert, Jul. 1997.
Vitafol® syrup product insert, 1997.
Vitafol®-PN product insert, 1997.
Select-OB™ product insert, Jul. 2005.
Agus et al., 17 Crit. Care Clin. 175-87 (2001).
Allman et al., 150 Med. J. Australia 130-33 (1999).
Anderson et al., 54 Am. J. Clin. Nutr. 909-916 (1991).
Anderson 26 Diabetes & Metabolism (Paris) 22-27 (2000).
Stoll, 87(3) Journal of Nutrition 193-198 (2002).
Bazzarre et al., 12(2) J. Amer. Coll. Nutr. 162-69 (1993).
Berendschot et al., 41 Invest. Ophthalmol. Vis. Sci. 3322-3326 (2000).
Bernstein et al., 72 Exp. Eye Res. 215-223 (2001).
Black, 85(2)(Supp.) Brit. J. Nutr. S193-S197 (2001).
Blumberg et al., 20(5) Clin. Nephrol. 244-50 (1983).
Bostom et al., 49(1) Kidney Int. 147-52 (1996).
Bothwell, 72(Supp.) Am. J. Clin. Nutr. 257S-64S (2000).
Braguer et al., 57 Nuphron 192-96 (1991).
Burk, 3 Biological Activity of Selenium 53-70 (1983).
Burton et al., Ann. NY Acad. Sci. 7-22 (1998).
Carr et al., 87 Circ. Res. 349-354 (2000).
Cattaneo, 32(Supp 1) Ann. Med. 46-52 (2000).
Chang et al., 51 Am. J. Clin. Nutr. 826-31 (1990).
Vanderput et al., Exp. Biol. Med. 243-70 (2001).
Christian et al., 130(11) J. Nutr. 2675-82 (2000).
Francois et al., 77 Am. J. Clin. Nutr. 226-33 (2003).
Von Schacky et al., 130(7) Annais of Internal Medicine 554-562 (1999).
Smuts et al., 101(3) The American College of Obstetricians and Gynecologists 469-479 (2003).
Uauy et al., 67 Amer. J. Clin. Nutr. 952S-959S (1998).
Cheruku et al., 76 Amer. J. Clin. Nutr. 608-613 (2002).
Kurnik et al., 37(11) Annals of Pharmacotherapy 1603-06 (2003).
Dawson-Hughes et al., 337 New Eng. J. Med. 670-76 (1997).
Day et al., 107(20) Circulation 2601-06 (2003).
DeFalco et al., 27 Clin. Exp. Obstet. Gynecol. 188-90 (2000).
Descombes et al., 24(10) Artifical Organs 773-78 (2000).
Dierkes et al., 11(2) J. Renal Nutr. 67-72 (2001).
Story et al., 27(1) Crit. Care Med. 220-23 (1999).
Stein et al., 3 Blood Purification 52-62 (1985).
Eskes, 27 Clin. Exp. Obstet. Gynecol. 157-67 (2000).
Facchietti et al., 9(1) European review for medical and pharmacological sciences 41-48 (2005).
Rioux et al., 95(2) Acta Paediatrica 137-144 (2006).
Fraker et al., Link Between Immune Status and Zinc Status 1399S-1406S (2000).
Hu et al., 287(14) JAMA 1815-1821 (2002).
Easterbauer et al., Free Rad. Biol. Med. 341-390 (1992).

(56) References Cited

OTHER PUBLICATIONS

Hanratty et al., 85 Heart 326-330 (2001).
Heller et al., 276 J. Biol. Chem. 40147 (2001).
Henkin et al., 91 Amer. J. Med. 239-246 (1991).
Henning et al., 95(9) Medizin Klinik 477-81 (2000).
Henriksen et al., 3(2) Arteriosclerosis 149-159 (1983).
Holben et al., 99(7) Journal of the American Dietetic Assoc. 836-843 (1999).
Hoogeveen et al., 101 Circulation 1509-1511 (2000).
Horrocks et al., 40(3) Pharmacological Research 211-225 (1999).
House et al., 45(1) ASAIO J. 94-97 (1999).
Huang et al., 275(23) J. Biol. Chem. 17399-17406 (2000).
Helland et al., 111 Pediatrics 39-44 (2003).
Islam et al., 150 Atherosclerosis 217-224 (2000).
Jaasveld et al., 99(1) Res. Comm. Mol. Pathol. Pharmacol. 69-80 (1988).
Vincent, 33(3) Sports Medicine 213-30 (2003).
Kagan et al., 44(8) Biochem. Pharmacol. 1637-1649 (1992).
Kang-Yoon et al., 56 Am. J. Chem. Nutr. 548-58 (1992).
Kharb, 93(1) Euro. J. Obstet Gynecol. Reprod. Biol. 37-39 (2000).
Kim, 57(10) Nutr. Reviews 314-21 (19990.
King, 71(Supp.) Am. J. Clin. Nutr. 13345-43S (2000).
Kishi et al., 48 Diabetes 2045-2051 (1999).
Lapido, 72( Supp.) Amer. J. Clin. Nutr. 280S-90S (2000).
Stevens et al., 59 Physiology & Behavior 915-920 (1996).
Lee et al., 58(3) Eur. J. Clin. Nutr. 481-7 (2004).
Lips et al., 86 J. Clin. Endocrinol. Metab. 1212-21 (2001).
Llurba et al., 37(4) Free Radic. Biol. Med. 557-70 (2004).
Lemke et al., 44 J. Lipid Res. 1591-1600 (2003).
Locksmith et al., 91(6) Obstet. Gynecol. 1027-34 (1998).
Shearer, 345 The Lancet 229-34 (1995).
Jurgensen et al., 31(1) LIPIDS 99-105 (1996).
Javaid et al., 367(9504) The Lancet 36-43 (2006).
Laidlaw et al., 77 Am. J. Clin. Nutr. 77:37-421 (2003).
Makoff, 25 Miner. Electrolyte Metab. 349-51 (1999).
Mares-Perlman et al., 153(5) Amer. J. Epidemiol. 424-432 (2001).
Naude et al., 40(12)Journal of Clinical Pharmacolgy 1447-51 (abstract only) (2000).
Neuringer et al., 44(9) Nutr. Rev. 285-94 (1986).
Maxwell, 95(Supp. 1) Basic Res. Cardiol. 66-71 (2000).
Schlaich et al., 153 Atherosclerosis 393-389 (2000).
DiStefano et al., 122(7) Gastroenterol. 1793-1799 (2002).
Milczarek et al., 210 Mol. Cell. Biochem. 65-73 (2000).
Monique DM Al et al., 71 Am. J. Clin. Nutr. 285S-291S (2000).
Morris et al., 13 J. Trace Elements Med. Biol. 57-61 (1999).
Moser-Veillon et al., 52 Am. J. Clin. Nutr. 135-41 (1990).
Myatt & Cui, 122(4) Histochem. Cell. Biol. 369-82 (2004).
Omenn et al., 334(18) New Eng. J. Med. 1150-1155 (1996).
O'Neil-Cutting et al., 255 JAMA 1468-1470 (1986).
The Vitatops Trial Study Group, 13 Cerebrovasc. Dis. 120-26 (2002).
Srinivas et al., 68(6) Indian J. Pediatr. 519-22 (2001).
Sifakis et al., 900 Ann. N.Y. Acad. Sci. 125-36 (2000).
Shechter et al., 102 Circulation 2353-58 (2000).
Frank et al., 70(4) Int. J. Vitam. Nutr, Res. 159-66 (2000).
Vitafol®-OB "Vitamin & mineral caplets for use before, during and after pregnancy", V1-May 5, 2002.
Order granting motion to stay litigation pending reexamination, Nov. 24, 2009.
1st Reexamination Request, Jul. 14, 2009.
Notice of Failure to Comply with *Ex Parte* Reexamination Request Filing Requirements, Jul. 27, 2009.
Reply to Notice of Failure to Comply with *Ex Parte* Reexamination Request Fling Requirements, Aug. 13, 2009.,
2nd Reexamination Request, Sep. 18, 2009.
Order Granting Reexamination, Oct. 23, 2009.
PDR for Nutritional Supplements, selected pages, 2001.
Pediatric Dental Health, May 22, 2004.
Perspectives in Nutrition, selected pages, 5th Edition, 2002.
Young et al., 45 Reprod. Nutr. Dev. 549-558 (2005).
Gey, 52 Bibl. Nutr. Dieta. 75-91 (1995).
Stampfer et al., 328 New Eng. J. Med. 1444-49 (1993).
Parker et al., 163(6) Am. J. Psychiatry 969-978 (2006).
Scholl et al., 146(2) Amer. J. Epidem. 134-41 (1997).
Haak et al., 108 Exp. Clin. Endocrinol. Diab. 168-174 (2000).
Haberland et al., 113(2) Amer. Heart J. 573-577 (1987).
Seager, 50 J. Phar. Pharmacol. 375-82 (1998).
Parfrey, 23 Advances in Nephrology 311-330 (1994).
Pema et al., 25 Mineral and Electrolyte Metabolism 95-99 (1999).
Purkkala Sarataho et al., 20 Arteriescler. Thromb, Vasc, Biol. 2087-2093 (2000).
Rapp et al., 41 Invest Ophthalmol. Vis. Sci. 1200-1209 (2000).
Shankar et al., 68 Amer. J. Clin. Nutr. 447S-463S (1998).
McNamara et al., 75(4-5) Prostaglandins Leukot Essent Fatty Acids 237-57 (2006).
Robinson et al., 94 Circulation 2743-48 (1996).
Rock et al., 96(7) J. Amer. Diet. Assoc. 693-702 (1996).
Rudich et al., 42 Dabetologia 949-957 (1999).
Otto et al., 69(4) Prostaglandins Leukot Essent Fatty Acids 237-43 (2003).
Mayne, 10 J. FASEB 690-701 (1996).
Shah et al., 10(1) Amer. J. Kidney Dis. 42-49 (1992).
Shah et al., 18(1) Amer. J. Kidney Dis. 84-90 (1991).
Reply Declaration of Lee P. Shulman, *Everett Laboratories, Inc.*, v. *Acella Pharmaceuticals, LLC*, Case No. 1:13- cv-03529-JEI-KMW (U.S. Dist. Ct. Dist. of NJ. Filed Aug. 16, 2013).
Exhibits A-B, to Lee P. Shulman Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Exhibit C, to Lee P. Shulman Reply Declaration, *Everett Laboratories, Inc.*, v. *Acella Pharmaceuticals, LLC*, Case No. 1:13-cv-03529-JEI-KMW (U.S. Dist. Ct. Dist. of Nj. Filed Aug. 16, 2013).
Exhibit D, to Lee P. Shulman Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Declaration of Yashoda V. Pramar, Ph.D., *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Supplemental Reply Declaration Part 1 of Jitka Shavel, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Supplemental Reply Declaration Part 2 of Jitka Shavel, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Declaration of Joseph Schramm, III, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Exhibit A-C, to Joseph Schramm, III, Declaration,*Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).
Opinion by Judge Joseph E. Irenas *Everett Laboratories, Inc.*, v. *Acella Pharmaceuticals, LLC*, Case No. 1:13-cv-03529-JEI-KMW (U.S. Dist. Ct. Dist. of NJ. Filed Aug. 29, 2013).
Order denying Plaintiffs Motion for Preliminary Injunction by Judge Joseph E. Irenas, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 29, 2013).
Everett Laboratories, Inc. Answer to Counterclaim *Everett Laboratories, Inc.*, v. *Acella Pharmaceuticals, LLC*, Case No. 1:13-cv-03529-Jei-Kmw (U.S. Dist. Ct. Dist. of NJ. Filed Sep. 3, 2013).
Amended Opinion on Everett's Motion to Preliminary Injunction by Judge Joseph Irenas, *Everett Laboratories, Inc.*, v. *Acella Pharmaceuticals, LLC*, Case No. 1:13-cv-03529-JEI-KMW (U.S. Dist. Ct. Dist. of NJ. Filed Sep. 13, 2013).
Complaint, *Everett Laboratories, Inc.*, v. *Acella Pharmaceuticals, LLC*, Case No. 2:33-av-00001 (U.S. Dist. Ct. Dist. of NJ. Filed Jun. 6, 2013).
Plaintiffs Proposed Order Granting Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

(56) References Cited

OTHER PUBLICATIONS

Brief in Support of Plaintiffs Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Declaration of Bruce Brown in Support of Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Declaration of Alisha Nielsen in Support of Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Declaration of Jitka Shavel in Support of Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Declaration of Lucas Sigman in Support of Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Declaration of Robert J. Schoenberg in Support of Motion for Preliminary Injunction, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 1-3, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 4-5, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 6-7, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 8-10, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 11-14, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 15-18, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Exhibits 19-30, to Robert J. Schoenberg Declaration, *Everett Laboratories, Inc.*, v. *Acella Pharmaceuticals, LLC*, Case No. 2:13-cv-03529-ES-SCM (U.S. Dist. Ct. Dist. of NJ. Filed Jul. 2, 2013).

Answer and Counterclaim of Defendent Acella Pharmaceuticals, LLC, *Everett Laboratories, Inc.*, v. *Acella Pharmaceuticals, LLC*, Case No. 1:13-cv-03529-JEI-KMW (U.S. Dist. Ct. Dist. of NJ. Filed Jul. 24, 2013).

Declaration of Mary M. Bridgeman, *Everett Laboratories, Inc.*, v. *Acella Pharmaceuticals, LLC*, Case No. 1:13- cv-03529-JEI-KMW (U.S. Dist. Ct. Dist. of NJ. Filed Aug. 8, 2013).

Exhibits A-F, to Mary M. Bridgeman Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Exhibits G-O, to Mary M. Bridgeman Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Exhibits P-S, to Mary M. Bridgeman Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Declaration of Harry G. Brittain, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Exhibits A-F, to Harry G. Brittain Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Exhibits G-S, to Harry G. Brittain Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Declaration of Bryce R. Cook, *Everett Laboratories, Inc.*, v. *Acella Pharmaceuticals, LLC*, Case No. 1:13-cv-03529-JEI-kMW (U.S. Dist. Ct. Dist. of NJ. Filed Aug. 8, 2013).

Exhibits A-B, to Bryce R. Cook Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Declaration of Harold Arthur Deas, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Exhibits A-C, to Harold Arthur Deas Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Declaration of Roger Beemer Newman, M.D., *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Exhibits A-E, to Roger Beemer Newman, M.D., Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 8, 2013).

Defendant Acella Pharmaceuticals, LLC's Memorandum in Opposition to Plaintiffs Motion for a Preliminary Injunction, *Everett Laboratories, Inc.*, v. *Acella Pharmaceuticals, LLC*, Case No. 1:13-cv-03529-JEI-KMW (U.S. Dist. Ct. Dist. of Nj. Filed Aug. 8, 2013).

Defendant Acella Pharmaceuticals, LLC's Amended Memorandum in Opposition to Plaintiffs Motion for a Preliminary Injunction, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 10, 2013).

Reply in Support of Plaintiffs Motion for Preliminary Injunction, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Reply Declaration of Lucas Sigman, in Support of Motion to Preliminary Injunction, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Exhibit A, to Lucas Sigman Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Exhibit B, to Lucas Sigman Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Exhibit C, to Lucas Sigman Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Exhibit D, to Lucas Sigman Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Reply Declaration of Robert J. Schoenberg, *Everett Laboratories, Inc.*, v. *Acella Pharmaceuticals, LLC*, Case No. 1:13- cv-03529-JEI-KMW (U.S. Dist. Ct. Dist. of NJ. Filed Aug. 16, 2013).

Exhibit 1, to Robert J. Schoenberg Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Exhibits 2, to Robert J. Schoenberg Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Exhibits 3-4, to Robert J. Schoenberg Reply Declaration, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Reply Declaration of Alisha Nielsen, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Reply Declaration of Bruce Brown, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

(56) References Cited

OTHER PUBLICATIONS

Reply Declaration of Brian C. Reisetter, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Reply Declaration of Douglas Gary Lichtman, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Reply Declaration of Walter Bratic, *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

Declaration of Lynn B. Bailey, Ph.D., *Everett Laboratories, Inc.*, v. *Acella Pharmaceuticals, LLC*, Case No. 1:13-cv-03529-JEI-KMW (U.S. Dist. Ct. Dist. of NJ. Filed Aug. 16, 2013).

* cited by examiner

KITS AND METHODS FOR NUTRITION SUPPLEMENTATION

CROSS REFERENCE TO RELATED APPLICATION

This application is a continuation and claims the benefit, under 35 U.S.C. §120, of U.S. patent application Ser. No. 12/422,091, filed Apr. 10, 2009, now U.S. Pat. No. 8,101,587, which is a continuation-in-part and claims the benefit, under 35 U.S.C. §120, of U.S. patent application Ser. No. 11/928,610, filed Oct. 30, 2007, now U.S. Pat. No. 8,197,855 which is a continuation and claims the benefit, under 35 U.S.C. §120, of U.S. patent application Ser. No. 10/916,534, filed Aug. 12, 2004, now U.S. Pat. No. 7,560,123. The entire contents and substance of these applications are hereby incorporated by reference.

FIELD OF THE INVENTION

The present invention relates to methods of co-administration of various vitamin and mineral compositions and kits provided for co-administration of these compositions for nutritional supplementation in, for example, subjects in physiologically stressful states.

BACKGROUND OF THE INVENTION

Nutrition plays a critical role in maintaining good health. Proper nutrition prevents dietary deficiencies, and also protects against the development of disease. When the body faces physiological stress, proper nutrition plays an increasingly important role. For example, pregnancy and lactation are among the most nutritionally volatile and physiologically stressful periods and processes in the lifetimes of women. Vitamin and mineral needs are almost universally increased during these natural processes. Increased vitamin and mineral needs during these times are almost always due to elevated metabolic demand, increased plasma volume, increased levels of blood cells, decreased concentrations of nutrients, and decreased concentrations of nutrient-binding proteins.

When increased nutrient needs occur during pregnancy, lactation, or any other physiologically stressful state, nutritional supplementation serves a vital role in maintaining good health. Nutritional supplementation is especially pertinent to women contemplating conceiving a child because optimizing specific nutrients before, during, and after the physiological processes of pregnancy or lactation can have profound, positive, and comprehensive impacts upon the overall wellness of the developing and newborn child as well as on the safety and health of the mother. The present invention provides kits and methods designed to supplement the nutritional needs of individuals in physiologically stressful states.

Supplementation with certain vitamins and minerals serves a role in protecting against disease and contributes to the overall health of the mother and developing child. Specifically, such compounds as vitamin $B_6$, vitamin $B_{12}$, vitamin $B_9$, and omega-3 fatty acids such as docosahexaenoic acid (DHA), play integral roles in physiological mechanisms that serve to prevent, treat and/or alleviate the occurrence or negative effects of some diseases.

DHA specifically has shown multiple health-promoting properties in adults. These include anti-thrombotic, anti-inflammatory and anti-atherosclerotic activity, all of which reduce the risk of heart disease. M Laidlaw and B J Holub, AM J CLIN NUTR 77:37-42 (2003). Inverse relationships have also been found between systemic levels of DHA and incidence and severity of mood disorders and depression, including post-partum depression. Therefore, introduction of omega-3 fatty acids such as DHA during pregnancy has a double benefit, to both child and mother.

Supplementation of other vitamins and minerals with DHA, however, may inhibit DHA's beneficial effects, for example, inhibiting the beneficial effects of reducing the incidence of post-partum depression. Indeed, high blood serum levels of copper, a mineral that is often included in nutritional supplements, has been associated with post-partum depression. J W Crayton et al., J TRACE ELEM MED BIOL 21(1): 17-21 (2007).

Other vitamins and minerals that provide certain benefits may also be associated with undesirable side effects, and thus, would preferably be excluded from a nutritional supplement. For example, calcium, a mineral that is often included in nutritional supplements, has been linked to constipation and other stomach problems such as nausea, vomiting and cramps.

A nutritional supplement kit for physiological stressful states such as during pregnancy or during lactation that includes the benefits of DHA, but excludes the vitamins and minerals that can either have deleterious effects on DHA's benefits, or other unappealing side effects, is currently needed.

SUMMARY OF THE INVENTION

The present invention provides methods of co-administering compositions and kits comprising compositions for both prophylactic and therapeutic nutritional supplementation. Specifically, for example, the present invention relates to novel compositions of vitamins and minerals that can be used to supplement the nutritional deficiencies observed in patients throughout physiologically stressful states. The present invention also may be formulated to exclude vitamins and minerals known to inhibit the beneficial effects of the included vitamins and minerals or cause other undesirable side effects.

The present invention includes methods of co-administering the compositions of the invention to patients, together or in any order, to supplement the nutritional deficiencies observed in patients throughout physiologically stressful states such as, for example, pregnancy, lactation, and any disease state. The compositions of the present invention may be in a swallowable, chewable or dissolvable form according to an individual patient's preference. Choice in dosage form promotes ease of administration and compliance with dosing regimens.

The present invention also includes kits that may be provided to patients, wherein the compositions as described herein are packaged for co-administration to a patient.

In one embodiment of the present invention, the methods may comprise co-administering to a patient a first composition comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc to a patient and a second composition comprising omega-3 fatty acids to the patient. In another embodiment, the methods and kits may comprise a second composition wherein omega-3 fatty acids comprise docahexaenoic acid (DHA). In another embodiment, the docahexaenoic acid is derived from algae.

In one embodiment, the methods may comprise co-administering the two compositions at the same time, or one after the other in either order. In a specific embodiment, the compositions of the described method may be co-administered to the patient orally.

In another specific embodiment of the methods and kits, the compositions may be swallowable, chewable, or dissolvable. In another embodiment, the first composition is in a different form than the second composition.

In another specific embodiment of the methods and kits of the present invention, vitamin A comprises acetate. In another specific embodiment, vitamin $B_1$ comprises thiamine mononitrate. In another specific embodiment, vitamin $B_3$ comprises niacinamide. In another specific embodiment, vitamin $B_6$ comprises pyridoxine hydrochloride. In another specific embodiment, vitamin $B_9$ comprises one or more of the group consisting of folic acid, folacin, metafolin, and folate. In another specific embodiment, vitamin $B_9$ comprises one or more natural derivatives of folate selected from the group consisting of (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof, and 5-formimino-(6S)-tetrahydrofolic acid or a polyglutamyl derivative thereof. In another specific embodiment, vitamin $B_{12}$ comprises cyanocobalamin. In another specific embodiment, vitamin C comprises ascorbic acid. In another specific embodiment, vitamin E comprises d-alpha tocopheryl acetate. In another specific embodiment, iron comprises polysaccharide iron complex. In another specific embodiment, magnesium comprises magnesium oxide. In another specific embodiment, zinc comprises zinc oxide.

In another specific embodiment of the methods and kits of the present invention, the first composition may be substantially free of one or more of added compounds selected from the group consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc.

In another embodiment of the methods and kits of the present invention, first and second compositions may be substantially free of one or more of added active compounds selected from the group consisting of lutein, lycopene, zeaxanthin, vitamin $B_4$, vitamin $B_5$, vitamin $B_7$, vitamin $B_8$, vitamin $B_{10}$, vitamin K, biotin, pantothenic acid, phosphorus, iodine, potassium, odorless garlic, coenzyme $Q_{10}$, l-carnitine, grape seed extract, chloride, sodium, green tea extract, quercetin, fluoride, hawthorne berries, and alpha lipoic acid. In another embodiment of the methods of the present invention, the first and second compositions may be substantially free of one or more of added minerals and compounds selected from the group consisting of, copper, calcium, chromium, titanium, molybdenum, nickel, tin, silicon, vanadium, manganese, selenium, selenite, boron, bismuth, borax, bauxite, gold, silver, hydroxylapatite, mica, quartz, steatite, talc, sulfur, and zircon. In another embodiment of the methods and kits of the present invention, the first and second compositions may be substantially free of one or more of added inactive compounds selected from the group consisting of magnesium stearate, silica, silicon dioxide, magnesium silicate, dicalcium phosphate, povidone, titanium dioxide, sodium benzoate, alpha lipoic acid, lutein, lycopene, cellulose, croscarmellose sodium, stearic acid, cellulose, hydroxylpropyl cellulose, hydroxypropyl methylcellulose, titanium dioxide, polydextrose, triacetin, dicalcium phosphate, polyethylene glycol, polyvinylpyrrolidone, mineral oil, methocel, sodium lauryl sulfate, and talc.

In another specific embodiment, the methods and kits may include a composition further comprising a pharmaceutically acceptable carrier. In another specific embodiment, the methods and kits may include the first composition further comprising a pharmaceutically acceptable carrier. In another specific embodiment, the methods and kits may include the second composition further comprising a pharmaceutically acceptable carrier. In another specific embodiment of the present invention, the pharmaceutically acceptable carrier is one or more selected from the group consisting of binders, diluents, lubricants, glidants, colorants, emulsifiers, disintegrants, starches, water, oils, alcohols, preservatives and sugars.

In another specific embodiment, the methods and kits may include the first composition further comprising a sweetening agent and the second composition further comprising a sweetening agent. In another specific embodiment, the first composition may further comprise a flavorant and the second composition further comprising a flavorant.

In another specific embodiment of the methods and kits of the present invention, the first composition may comprise about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; and about 7.0 mg to about 23 mg of zinc. In another specific embodiment of the methods and kits of the present invention, the first composition may comprise about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; and about 15 mg of zinc.

In another specific embodiment of the methods and kits of the present invention, omega-3 fatty acids may be present in the amount of about 125 mg to about 375 mg. In another embodiment, omega-3 fatty acids may be present in the amount of about 200 mg to about 300 mg. In another embodiment, omega-3 fatty acids may be present in the amount of about 225 mg to about 275 mg. In another embodiment, omega-3 fatty acids may be present in the amount of about 250 mg. In another embodiment, the omega-3 fatty acids may be enclosed within a gel-cap. In another embodiment, the second composition may be in liquid form.

In another embodiment of the present invention the kits may comprise: a first composition comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and a second composition comprising omega-3 fatty acids; wherein the first and second compositions are packaged for co-administration to a patient, in any order.

In another embodiment, the kits are packaged in various forms including bottles and blister packs.

In yet another embodiment, the kits may be packaged in bottles that are sold together; one bottle containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and one bottle containing compositions comprising omega-3 fatty acids such as DHA.

In yet another embodiment, the kits may be packaged in bottles that are sold separately; one bottle containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and one bottle containing compositions comprising omega-3 fatty acids such as DHA.

In an alternative embodiment, the kits may be packaged in bottles advertised as more effective if co-administered; one bottle containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and one bottle containing compositions comprising omega-3 fatty acids such as DHA. The advertisements may consist of internet, print, and product packaging advertisements.

In another embodiment, the kits may be packaged in blister packs that are sold together: one blister pack containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and one blister pack containing compositions comprising omega-3 fatty acids such as DHA.

In yet another embodiment, the kits may be packaged in one blister pack: containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and containing compositions comprising omega-3 fatty acids such as DHA.

In another embodiment, the kits may be packaged in blister packs that are sold separately; one blister pack containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and one blister pack containing compositions comprising omega-3 fatty acids such as DHA.

In yet another embodiment, the kits may be packaged in blister packs advertised as more effective if co-administered: one blister pack containing compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and one blister pack containing compositions comprising omega-3 fatty acids such as DHA. The advertisements may consist of internet, print, and product packaging advertisements.

In another embodiment, the invention comprises a method which comprises providing the kit as described to patients.

In one embodiment of the present invention, the methods may comprise co-administering to a patient a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc and one or more pharmaceutically acceptable carriers to a patient; and a second composition consisting of DHA and one or more pharmaceutically acceptable carriers to said patient. In another embodiment, the first composition may consist of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc and one or more pharmaceutically acceptable carriers; and the second composition may consist of about 125 mg to about 375 mg of DHA and one or more pharmaceutically acceptable carriers. In another embodiment, the first composition may consist of about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; about 15 mg of zinc and one or more pharmaceutically acceptable carriers; and the second composition may consist of about 250 mg of DHA and one or more pharmaceutically acceptable carriers.

In another embodiment of the present invention, the kits may comprise: a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc and one or more pharmaceutically acceptable carriers; and a second composition consisting of DHA and one or more pharmaceutically acceptable carriers; wherein the first and second compositions are packaged for administration to a patient, in any order. In another embodiment, the first composition may consist of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc and one or more pharmaceutically acceptable carriers; and the second composition may consist of about 125 mg to about 375 mg of DHA and one or more pharmaceutically acceptable carriers. In another embodiment, the first composition may consist of about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; about 15 mg of zinc and one or more pharmaceutically acceptable carriers; and the second composition may consist of about 250 mg of DHA and one or more pharmaceutically acceptable carriers. In another embodiment, the invention comprises a method which comprises providing the kit as described to patients.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, fillers, and excipients, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a vitamin" is a reference to one or more vitamins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention. All references cited herein are incorporated by reference herein in their entirety.

The term "disease state" as used herein, may comprise any state in which one or more organs or components of an organism malfunction. The term "disease state" may refer to any deterioration of any component of a body. The term "disease state" may refer to any deficiency of any compound necessary for the maintenance or function of any component of any organism. The term "disease state" may refer to any condition in which a body contains toxins, produced by microorganisms that infect the body or by body cells through faulty metabolism or absorbed from an external source. "Disease states" may be adverse states caused by any diet, any virus, or any bacteria. "Disease states" may comprise disorders associated with pregnant females such as, for example, osteomalacia and preeclampsia and disorders associated with a fetus such as, for example, neural tube defects and various fetal abnormalities. "Disease states" may comprise any pulmonary disorder such as, for example, bronchitis, bronchiectasis, atelectasis, pneumonia, diseases caused by inorganic dusts, diseases caused by organic dusts, any pulmonary fibrosis, and pleurisy. "Disease states" may comprise any hematological/oncological disorder such as, for example, anemia, hemophilia, leukemia, and lymphoma. A "disease state" may comprise any cancer such as, for example, breast cancer, lung cancer, prostate cancer, pancreatic cancer, liver cancer, stomach cancer, testicular cancer, ovarian cancer, skin cancer, cancer of the brain, cancer of the mouth, cancer of the throat, and cancer of the neck. "Disease states" may comprise any disorder of the immune system such as, for example, acquired immune deficiency syndrome (AIDS), AIDS-related complex, infection by any strain of any human immunodeficiency virus (HIV), and other viruses or pathogens such as bacteria, fungi and parasites. A "disease state" may comprise any cardiovascular disorder such as, for example, arterial hypertension, orthostatic hypotension, arteriosclerosis, coronary artery disease, cardiomyopathy, any arrhythmia, any valvular heart disease, endocarditis, pericardial disease, any cardiac tumor, any aneurysm, and any peripheral vascular disorder. "Disease states" may comprise any hepatic/biliary disorder such as, for example, jaundice, hepatic steatosis, fibrosis, cirrhosis, hepatitis, any hepatic granuloma, any liver tumor, cholelithiasis, cholecystitis, and choledocholithiasis.

The term "physiologically stressful state," as used herein, comprises any state of an organism in which the organism faces one or more physiological challenges. A "physiologically stressful state" may comprise pregnancy, lactation, or conditions in which an organism faces physiological challenges related to, for example, elevated metabolic demand, increased plasma volume, or decreased concentrations of nutrient-binding proteins. A "physiologically stressful state" may result from one or more disease states.

The term "subject," as used herein, comprises any and all organisms and includes the term "patient." "Subject" may refer to a human or any other animal. "Subject" may also refer to a fetus.

The phrase "co-administration" refers to administration of two compositions to a patient together or within a certain desired time.

The phrase "chewable form" refers to any relatively soft compositions that are chewed in the mouth after oral administration, have a pleasant taste and mouthfeel, and quickly break into smaller pieces and begin to dissolve after chewing such that they can be swallowed substantially as a solution.

The phrase "dissolvable form" refers to any compositions that dissolve into a solution in the mouth. Such compositions, in one embodiment, may dissolve within about 60 seconds or less after placement in the mouth without any chewing.

The term "mouthfeel" refers to non-taste-related aspects of the pleasantness experienced by a person while chewing or swallowing a nutritional supplement. Aspects of mouthfeel include, for example and without limitation, the hardness and brittleness of a composition, whether the composition is chewy, gritty, oily, creamy, watery, sticky, easily dissolved, astringent, effervescent, and the like, and the size, shape, and form of the composition (tablet, powder, gel, etc.).

The term "antioxidant" means an agent which inhibits oxidation and thus is used to prevent deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and others known to those of ordinary skill in the art.

The phrase "pharmaceutically acceptable," as used herein, refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Thus, the phrase "pharmaceutically acceptable carriers," as used herein, refers to such suitable compounds and materials defined above that may be added to the dosage form to assist in satisfactory processing of the dosage form or provide desirable physical characteristics to the dosage form. For example, "pharmaceutically acceptable carriers" may include, but is not limited to, binders, diluents, lubricants, glidants, colorants, emulsifiers, disintegrants, starches, water, oils, alcohols, preservatives, and sugars. In another example, "pharmaceutically acceptable carriers" refers to dosage forms such as gel-caps used with, for example, the compositions of the present invention comprising or consisting of omega-3 fatty acids such as docosahexaenoic acid (DHA). Thus, "pharmaceutically acceptable carriers" in gel-caps may be in for example, liquid or oil form, and may include a filler or other appropriate liquid vehicle and may be used with omega-3 fatty acids such as docosahexaenoic acid (DHA).

The phrase "swallowable form" refers to any compositions that do not readily dissolve when placed in the mouth and may be swallowed whole without any chewing or discomfort. Such compositions, in one embodiment, may have a shape containing no sharp edges and a smooth, uniform and substantially bubble free outer coating.

The term "dosage form," as used herein, is the form in which the dose is to be administered to the subject or patient. The drug or supplement is generally administered as part of a formulation that includes nonmedical agents. The dosage form has unique physical and pharmaceutical characteristics. Dosage forms may be solid, liquid or gaseous. Solid forms include, but are not limited to pills, capsules, tablets, gel caplets, softgels, lozenges, wafers etc.

The term "substantially free of added" as used herein, means free from therapeutically effective amounts of compounds when administered in suggested doses, but may include trace amounts of compounds in non-therapeutically effective amounts. For example, a composition of the present invention that included an inactive ingredient that is a salt or compound including a mineral would still be substantially free of added minerals.

As used herein, the terms "inactive," "inert," "excipient," and/or "formulatory" refer to any compound that is an inactive ingredient of a described composition. The definition of "inactive ingredient" as used herein follows that of the U.S. Food and Drug Administration, as defined in 21 C.F.R. 201.3 (b)(8), which is any component of a drug product other than the active ingredient.

By "active ingredient," then, is meant any compound intended to furnish pharmacological activity or other direct effect in the diagnosis, cure, mitigation, treatment and/or prevention of a condition. See 21 C.F.R. 210.3(b)(7). Further, "active ingredients" include those compounds of the composition that may undergo chemical change during the manufacture of the composition and be present in the final composition in a modified form intended to furnish an activity or effect. Id.

The term "administrable" defines a composition that is able to be given to a patient. Likewise, "administering" refers to the act of giving a composition to a patient or otherwise making such composition available to a patient or the patient taking a composition.

As used herein, the term "about," when located before a dosage amount or dosage range of a specific ingredient, refers to an amount or range closely above and/or closely below the stated amount or range that does not manifestly alter the therapeutic effect of the specific ingredient from the stated amount or range.

Proper nutrition is essential for maintaining health and preventing diseases. Adequate nutrition is especially critical during, for example, nutritionally volatile or physiologically stressful periods such as those including, by way of example and without limitation, pregnancy, lactation, or any disease state. Vitamin and mineral needs are almost universally increased throughout these periods. Increased needs during physiologically stressful states such as pregnancy, lactation or disease state may result from elevated metabolic demand, increased plasma volume, increased quantities of circulating red blood cells, decreased concentrations of nutrients, and decreased concentrations of nutrient-binding proteins such as, for example and without limitation, serum-ferritin, maltose-binding protein, lactoferrin, calmodulin, tocopheryl binding protein, riboflavin binding protein, retinol binding protein, transthyretin, high density lipoprotein-apolipoprotein A1, folic acid binding protein, and 25-hydroxyvitamin D binding protein. Lapido, 72 (Supp.) AMER. J. CLIN. NUTR. 280S-90S (2000).

Optimizing specific nutrients before, during, and after the physiological processes of pregnancy and lactation can have profound, positive, and comprehensive impacts on the overall wellness of the developing and newborn child as well as on the safety and health of the mother. Black, 85 (Supp.) BRIT. J. NUTR. S193-97 (2001); Scholl et al., 146 AMER. J. EPIDEM. 134-41 (1997). Nutrients provided to a mother reach the fetus. Specifically, it is established that substrates for growth and development, for example, circulate within the same pathways that carry drugs to and waste products from the fetus. Exchanges of material between mother and fetus occur primarily in the placenta, where villi containing fetal capillaries protrude into sinuses (intervillous spaces). Maternal arterial blood spurts into these spaces, then drains into maternal uterine veins to be returned to the maternal systemic circulation. Solutes in maternal blood cross the epithelial cells and connective tissue of the villi and the endothelium of the fetal capillaries; these solutes are then carried to the fetus by placental veins, which converge into the umbilical vein. THE MERCK MANUAL OF DIAGNOSIS AND THERAPY 2022 (Mark H. Beers, M. D. & Robert Berkow, M. D., eds., 17th ed. 1999).

The kits and methods of the present invention provide the means to optimize good health by utilizing vitamin and mineral nutritional supplementation. The kits and methods of the present invention may be administered to or directed to a subject such as a human or any other organism.

The compositions of the kits and methods of the present invention may include vitamin A. Vitamin A is involved in physiological processes that result in cellular differentiation, cellular maturity, and cellular specificity. Thus, vitamin A is an important component of a nutritional supplement for subjects in physiologically stressful states, such as those caused by pregnancy, lactation or disease state. Zile et al., 131(3) J. NUTR. 705-08 (2001). Care should be taken, however, to avoid excess. Indeed, supplemental vitamin A ingestion during pregnancy has been shown in some studies to be teratogenic or deforming to human and animal embryos. G B Mulder et al., 62(4) TERATOLOGY 214-26 (2000). Thus, in a specific embodiment of the invention, vitamin A may be included in amounts ranging from about 550 IU to about 1650 IU. In another specific embodiment, vitamin A may be included in amounts ranging from about 880 IU to about 1320 IU. In another specific embodiment, vitamin A may be included in amounts ranging from about 990 IU to about 1210 IU. In another embodiment, vitamin A may be included in an amount of about 1100 IU.

In a specific embodiment of the present invention, vitamin A may be included in the form of acetate. In another specific embodiment, vitamin A in the form of acetate may be included in amounts ranging from about 550 IU to about 1650 IU. In another specific embodiment, vitamin A in the form of acetate may be included in amounts ranging from about 880 IU to about 1320 IU. In another specific embodiment, vitamin A in the form of acetate may be included in amounts ranging from about 990 IU to about 1210 IU. In another embodiment, vitamin A in the form of acetate may be included in an amount of about 1100 IU.

The compositions of the kits and methods of the present invention may include beta carotene. Beta carotene is converted to vitamin A within the body as needed. Mayne, 10 J. FASEB 690-701 (1996). Beta carotene also has powerful anti-oxidant properties. Antioxidants are important during physiologically stressful events for numerous reasons. For example, lipid peroxidation has been associated with over 200 disease processes. Rock et al., 96(7) J. AMER. DIET. ASSOC. 693-702 (1996). Antioxidants are especially important during pregnancy because in the first trimester, establishment of blood flow into the intervillous space is associated with a burst of oxidative stress. The inability to mount an effective antioxidant defense against this burst results in early pregnancy loss. Myatt & Cui, 122, HISTOCHEM. CELL BIOL., 369-82 (2004). Further, oxidative stress has been implicated in the pathophysiology of preeclampsia, a toxemia of pregnancy. Llurba et al., 37(4) FREE RADIC. BIOL. MED. 557-70 (2004). Finally, oxidative stress during pregnancy plays an important role in fetal growth, and healthy antioxidant levels are positively correlated with birth weight and length. Myatt & Cui; Lee et al., 58 EUR. J. CLIN. NUTR., 481-87 (2004).

In a specific embodiment of the present invention, beta carotene may be included in amounts ranging from about 300 IU to about 900 IU. In another specific embodiment of the present invention, beta carotene may be included in amounts ranging from about 480 IU to 720 IU. In another specific embodiment of the present invention, beta carotene may be included in amounts ranging from about 540 IU to about 660 IU. In another embodiment, beta carotene may be included in an amount of about 600 IU.

The compositions of the kits and methods of the present invention may comprise or use B-complex vitamins. This class of vitamins comprises water-soluble nutrients generally not stored in the body. They play roles in a variety of biological processes critical to the health of pregnant women, lactating women, and fetuses such as, for example, the metabolism of homocysteine. The B-complex vitamins that may be included in the kits and methods of the present invention comprise one or more of vitamin $B_1$, vitamin $B_2$, vitamin $B_3$, vitamin $B_6$, vitamin $B_9$ and vitamin $B_{12}$.

The compositions of the kits and methods of the present invention may comprise or use vitamin $B_1$. Vitamin $B_1$ plays a role in carbohydrate metabolism and neural function. It is a coenzyme for the oxidative decarboxylation of alpha-ketoacids (e.g., alpha-ketoglutarate and pyruvate) and for transketolase, which is a component of the pentose phosphate pathway. NATIONAL RESEARCH COUNCIL, RECOMMENDED DIETARY ALLOWANCES 123 (10th ed. 1989) (hereinafter "RDA"). In a specific embodiment of the present invention, vitamin $B_1$ may be included in the form of thiamine mononitrate. In another specific embodiment, vitamin $B_1$ may be included in amounts ranging from about 1.0 mg to about 3.0 mg. In another specific embodiment, vitamin $B_1$ may be included in amounts ranging from about 1.3 mg to about 1.9 mg. In another specific embodiment, vitamin $B_1$ may be included in amounts ranging from about 1.5 mg to about 1.75 mg. In another embodiment, vitamin $B_1$ may be included in an amount of about 1.6 mg.

In another specific embodiment, vitamin $B_1$ in the form of thiamine mononitrate may be included in amounts ranging from about 1.0 mg to about 3.0 mg. In another specific embodiment, vitamin $B_1$ in the form of thiamine mononitrate may be included in amounts ranging from about 1.3 mg to about 1.9 mg. In another specific embodiment, vitamin $B_1$ in the form of thiamine mononitrate may be included in amounts ranging from about 1.5 mg to about 1.75 mg. In another embodiment, vitamin $B_1$ in the form of thiamine mononitrate may be included in an amount of about 1.6 mg.

The compositions of the kits and methods of the present invention may comprise or use vitamin $B_2$. Vitamin $B_2$ is a component of two flavin coenzymes, flavin mononucleotide (FMN) and flavin adenine dinucleotide (FAD). These flavoenzymes are involved in a number of oxidation-reduction reactions including the conversion of pyridoxine and niacin. RDA, supra at 132. Flavoenzymes also play a role in a number of metabolic pathways such as amino acid deamination, purine degradation and fatty acid oxidation and thus help to maintain carbohydrate, amino acid and lipid metabolism. In a specific embodiment of the present invention, vitamin $B_2$ may be included in the form of riboflavin.

In another specific embodiment, vitamin $B_2$ may be included in amounts ranging from about 1 mg to about 3 mg. In another specific embodiment, vitamin $B_2$ may be included in amounts ranging from about 1.5 mg to about 2.2 mg. In another specific embodiment, vitamin $B_2$ may be included in amounts ranging from about 1.6 mg to about 2 mg. In another embodiment, vitamin $B_2$ may be included in an amount of about 1.8 mg.

In another specific embodiment, vitamin $B_2$ in the form of riboflavin may be included in amounts ranging from about 1 mg to about 3 mg. In another specific embodiment, vitamin $B_2$ in the form of riboflavin may be included in amounts ranging from about 1.5 mg to about 2.2 mg. In another specific embodiment, vitamin $B_2$ in the form of riboflavin may be included in amounts ranging from about 1.6 mg to about 2 mg. In another embodiment, vitamin $B_2$ in the form of riboflavin may be included in an amount of about 1.8 mg.

The compositions of the kits and methods of the present invention may comprise or use vitamin $B_3$. Vitamin $B_3$, or "niacin" is the common name for two compounds: nicotinic acid (also called niacin) and niacinamide (also called nicotinamide). Vitamin $B_3$ is particularly important for maintaining healthy levels and types of fatty acids. It is also required for the synthesis of pyroxidine, riboflavin, and folic acid. RDA, supra at 137. Administration of vitamin $B_3$ also may effect a reduction in total cholesterol (LDL) and very low density lipoprotein (VLDL) levels and an increase in high density lipoprotein (HDL) cholesterol levels. Nicotinamide adenine dinucleotide (NAD) and NAD phosphate (NADP) are active coenzymes of niacin. These coenzymes are involved in numerous enzymatic reactions such as glycolysis, fatty acid metabolism, and steroid synthesis. Henkin et al., 91 AM. J. MED. 239-46 (1991). In a specific embodiment of the present invention, vitamin $B_3$ may be included in the form of niacinamide. In another specific embodiment, the present invention may include an equivalent molar amount of niacin. In another specific embodiment, vitamin $B_3$ may be included in amounts ranging from about 7 mg to about 23 mg. In another specific embodiment, vitamin $B_3$ may be included in amounts ranging from about 12 mg to about 18 mg. In another specific embodiment, vitamin $B_3$ may be included in amounts ranging from about 13.5 mg to about 16.5 mg. In another embodiment, vitamin $B_3$ may be included in an amount of about 15 mg.

In another specific embodiment, vitamin $B_3$ in the form of niacinamide may be included in amounts ranging from about 7 mg to about 23 mg. In another specific embodiment, vitamin $B_3$ in the form of niacinamide may be included in amounts ranging from about 12 mg to about 18 mg. In another specific embodiment, vitamin $B_3$ in the form of niacinamide may be included in amounts ranging from about 13.5 mg to about 16.5 mg. In another embodiment, vitamin $B_3$ in the form of niacinamide may be included in an amount of about 15 mg.

The compositions of the kits and methods of the present invention may comprise or use vitamin $B_6$. The administration of vitamin $B_6$ may reduce the levels of homocysteine. Bostom et al., 49 KIDNEY INT. 147-52 (1996). The active forms of vitamin $B_6$, pyridoxal-5'-phosphate (PLP) and pyridoxamine-5'-phosphate, are coenzymes for numerous enzymes and as such, are important for gluconeogenesis, niacin formation, and erythrocyte metabolism. RDA, supra at 142-43. Vitamin $B_6$ is a coenzyme for both cystathionine synthase and cystathionase, enzymes that catalyze the formation of cysteine from methionine. Homocysteine is an intermediate in this process and elevated levels of plasma homocysteine are recognized as a risk factor for both vascular disease (Robinson et al., 94 CIRCULATION 2743-48 (1996)) and neural tube defects (Locksmith & Duff, 91 OBSTET. GYNECOL. 1027-34 (1998)). In a specific embodiment of the present invention, vitamin $B_6$ may be included in the form of pyridoxine hydrochloride. In another specific embodiment, vitamin $B_6$ may be included in amounts ranging from about 1 mg to about 4 mg. In another specific embodiment, vitamin $B_6$ may be included in amounts ranging from about 2 mg to about 3 mg. In another specific embodiment, vitamin $B_6$ may be included in amounts ranging from about 2.3 mg to about 2.8 mg. In another embodiment, vitamin $B_6$ may be included in an amount of about 2.5 mg.

In another specific embodiment, vitamin $B_6$ in the form of pyridoxine hydrochloride may be included in amounts ranging from about 1 mg to about 4 mg. In another specific embodiment, vitamin $B_6$ in the form of pyridoxine hydrochloride may be included in amounts ranging from about 2 mg to about 3 mg. In another specific embodiment, vitamin $B_6$ in the form of pyridoxine hydrochloride may be included in amounts ranging from about 2.3 mg to about 2.8 mg. In another embodiment, vitamin $B_6$ in the form of pyridoxine hydrochloride may be included in an amount of about 2.5 mg.

The compositions of the kits and methods of the present invention may comprise or use vitamin $B_9$. This vitamin has demonstrated the ability to prevent neural tube defects such as spina bifida caused by disturbed homocysteine metabolism. Vanderput et al., EXP. BIOL. MED. 243-70 (2001); DeFalco et al., 27 CLIN. EXP. OBSTET. GYNECOL. 188-90 (2000); Eskes, 27 CLIN. EXP. OBSTET. GYNECOL. 157-67 (2000); Locksmith & Duff, supra. Vitamin $B_9$ also is important for the formation of red and white blood cells within bone marrow and plays a role in heme formation. Further, folate deficiencies inhibit the activity of vitamin $B_1$. RDA, supra at 150. In a specific embodiment of the present invention, vitamin $B_9$ may be included in the form of folic acid. In another embodiment, vitamin $B_9$ may be included in the forms of folic acid, folacin, metafolin, folate and/or one or more natural isomers of folate including (6S)-tetrahydrofolic acid or a polyglutamyl derivative thereof, 5-methyl-(6S)-tetrahydrofolic acid or a polyglutamyl derivative thereof, 5-formyl-(6S)-tetrahydrofolic acid or a polyglutamyl derivative thereof, 10-formyl-(6R)-tetrahydrofolic acid or a polyglutamyl derivative thereof, 5,10-methylene-(6R)-tetrahydrofolic acid or a polyglutamyl derivative thereof, 5,10-methenyl-(6R)-tetrahydrofolic acid or a polyglutamyl derivative thereof and 5-formimino-(6S)-tetrahydrofolic acid or a polyglutamyl derivative thereof. In a specific embodiment, vitamin $B_9$ may be in the form of pteroylglutamic acid. In another specific embodiment, vitamin $B_9$ may be included in amounts ranging from about 500 µg to about 1500 µg. In another specific embodiment, vitamin $B_9$ may be included in amounts ranging from about 800 µg to about 1200 µg. In another specific embodiment, vitamin $B_9$ may be included in amounts ranging from about 900 µg to about 1100 µg. In another embodiment, vitamin $B_9$ may be included in an amount of about 1000 µg.

In another specific embodiment, vitamin $B_9$ in the form of folic acid may be included in amounts ranging from about 500 µg to about 1500 µg. In another specific embodiment, vitamin $B_9$ in the form of folic acid may be included in amounts ranging from about 800 µg to about 1200 µg. In another specific embodiment, vitamin $B_9$ in the form of folic acid may be included in amounts ranging from about 900 µg to about 1100 µg. In another embodiment, vitamin $B_9$ in the form of folic acid may be included in an amount of about 1000 µg.

The compositions of the kits and methods of the present invention may comprise or use vitamin $B_{12}$. Vitamin $B_{12}$ can be converted to the active coenzymes, methylcobalamin and 5'-deoxyadenosylcobalamin. These coenzymes are necessary for folic acid metabolism, conversion of coenzyme A and myelin synthesis. Methylcobalamin also catalyzes the demethylation of a folate cofactor which is involved in DNA synthesis. A lack of demethylation may result in folic acid deficiency. RDA, supra at 159-160. Deoxyadenosylcobalamin is the coenzyme for the conversion of methylmalonyl-CoA to succinyl-CoA, which plays a role in the citric acid cycle. Cobalamin, along with pyridoxine and folic acid, also are implicated in the proper metabolism of homocysteine, a breakdown product of the amino acid methionine, which is correlated with an increased risk of heart disease due to its negative effects on endothelial function. In one specific embodiment of the present invention, vitamin $B_{12}$ may be included in the form of cyanocobalamin. In another specific embodiment, vitamin $B_{12}$ may be included in amounts ranging from about 2 µg to about 8 µg. In another specific embodiment, vitamin $B_{12}$ may be included in amounts ranging from about 4 µg to about 6 µg. In another specific embodiment, vitamin $B_{12}$ may be included in amounts ranging from about 4.5 µg to about 5.5 µg. In another embodiment, vitamin $B_{12}$ may be included in an amount of about 5 µg.

In another specific embodiment, vitamin $B_{12}$ in the form of cyanocobalamin may be included in amounts ranging from about 2 µg to about 8 µg. In another specific embodiment, vitamin $B_{12}$ in the form of cyanocobalamin may be included in amounts ranging from about 4 µg to about 6 µg. In another specific embodiment, vitamin $B_{12}$ in the form of cyanocobalamin may be included in amounts ranging from about 4.5 µg to about 5.5 µg. In another embodiment, vitamin $B_{12}$ in the form of cyanocobalamin may be included in an amount of about 5 µg.

The compositions of the kits and methods of the present invention may comprise or use vitamin C. The major biochemical role of water-soluble vitamin C is as a co-substrate in metal catalyzed hydroxylations. Like beta carotene, vitamin C has antioxidant properties. It interacts directly with superoxide hydroxyl radicals and singlet oxygen, and also provides antioxidant protection for folate and vitamin E, keeping vitamin E in its most potent form. Vitamin C may afford protective effects against preeclampsia by participating in the scavenging of free radicals. Indeed, significantly lower levels of vitamin C have been observed in preeclamptic women than in controls. Woods et al., 185(1) AM. J. OBSTET. GYNECOL. 5-10 (2001); Kharb, 1 EURO. J. OBSTET. GYNECOL. REPRO. BIOL. 37-39 (2000); Milczarek et al., 210 MOL. CELL. BIOCHEM. 65-73 (2000). Vitamin C also enhances the absorption of iron. RDA, supra at 115. In addition, vitamin C is required for collagen synthesis, epinephrine synthesis, and bile acid formation. Moreover, vitamin C has been implicated in inhibiting atherosclerosis by being present in extracellular fluid of the arterial wall and potentiating nitric oxide activity, thus normalizing vascular function. In a specific embodiment of the present invention, vitamin C may be included in the form of ascorbic acid. In another specific embodiment, vitamin C may be included in amounts ranging from about 30 mg to about 90 mg. In another specific embodiment, vitamin C may be included in amounts ranging from about 48 mg to about 72 mg. In another specific embodiment, vitamin C may be included in amounts ranging from about 54 mg to about 66 mg. In another embodiment, vitamin C may be included in an amount of about 60 mg.

In another specific embodiment, vitamin C in the form of ascorbic acid may be included in amounts ranging from about 30 mg to about 90 mg. In another specific embodiment, vitamin C in the form of ascorbic acid may be included in amounts ranging from about 48 mg to about 72 mg. In another specific embodiment, vitamin C in the form of ascorbic acid may be included in amounts ranging from about 54 mg to about 66 mg. In another embodiment, vitamin C in the form of ascorbic acid may be included in an amount of about 60 mg.

The compositions of the kits and methods of the present invention may comprise or use vitamin $D_3$. Vitamin $D_3$ is a fat-soluble "hormone like" substance important for the maintenance of healthy bones. This vitamin increases the absorption of calcium and phosphorous from the gastrointestinal tract, and improves mineral resorption into bone tissue. Vitamin D can be converted to its active form from exposure of the skin to sunlight. This fact is among the reasons why vitamin D deficiency is common in the elderly, notably the institutionalized, who spend little or no time out of doors. Deficiencies in vitamin $D_3$ can lead to increased bone turnover and loss, and when severe, osteomalacia, or softening of the bones. Supplementation with vitamin $D_3$ has been shown to moderately reduce bone loss, increase serum 25-hydroxyvitamin D, and decrease serum parathyroid hormone levels. Dawson-Hughes et al., 337 NEW ENG. J. MED. 670-76 (1997); Lips et al., 86 J. CLIN. ENDOCRINOL. METAB. 1212-21 (2001). Vitamin $D_3$ also plays a role in the maintenance of calcium and phosphorus homeostasis, but it is also active in cell differentiation and immune function. In a specific embodiment of the present invention, vitamin $D_3$ may be included in the form of cholecalciferol. In another specific embodiment, vitamin $D_3$ may be included in amounts ranging from about 200 IU to about 600 IU. In another specific embodiment, vitamin $D_3$ may be included in amounts ranging from about 320 IU to about 480 IU. In another specific embodiment, vitamin $D_3$ may be included in amounts ranging from about 360 IU to about 440 IU. In another embodiment, vitamin $D_3$ may be included in an amount of about 400 IU.

In another specific embodiment, vitamin $D_3$ in the form of cholecalciferol may be included in amounts ranging from about 200 IU to about 600 IU. In another specific embodiment, vitamin $D_3$ in the form of cholecalciferol may be included in amounts ranging from about 320 IU to about 480 IU. In another specific embodiment, vitamin $D_3$ in the form of cholecalciferol may be included in amounts ranging from about 360 IU to about 440 IU. In another embodiment, vitamin $D_3$ in the form of cholecalciferol may be included in an amount of about 400 IU.

The compositions of the kits and methods of the present invention may comprise or use vitamin E. Vitamin E is a fat-soluble vitamin antioxidant found in biological membranes where it protects the phospholipid membrane from oxidative stress. Vitamin E inhibits the oxidation of unsaturated fatty acids by trapping peroxyl free radicals. It is also an antiatherogenic agent, and studies have demonstrated a reduced risk of coronary heart disease with increased intake of vitamin E. Stampfer et al., 328 NEW ENG. J. MED. 1444-49 (1993). In addition, vitamin E, like beta carotene and vitamin C, may afford protective effects against preeclampsia by participating in the scavenging of free radicals. As with vitamin C, significantly lower levels of vitamin E have been observed in preeclamptic women than in controls. Woods et al., supra; Kharb, supra; Milczarek et al., supra. In a specific embodiment of the present invention, vitamin E may be included in the form of d-alpha-tocopheryl acetate. In another specific embodiment, vitamin E may be included in the form of an equivalent molar amount of d-alpha tocopheryl succinate. In another specific embodiment, vitamin E may be included in amounts ranging from about 15 IU to about 45 IU. In another specific embodiment, vitamin E may be included in amounts ranging from about 24 IU to about 36 IU. In another specific embodiment, vitamin E may be included in amounts ranging from about 27 IU to about 33 IU. In another embodiment, vitamin E may be included in an amount of about 30 IU.

In another specific embodiment, vitamin E in the form of d-alpha-tocopheryl acetate may be included in amounts ranging from about 15 IU to about 45 IU. In another specific embodiment, vitamin E in the form of d-alpha-tocopheryl acetate may be included in amounts ranging from about 24 IU to about 36 IU. In another specific embodiment, vitamin E in the form of d-alpha-tocopheryl acetate may be included in amounts ranging from about 27 IU to about 33 IU. In another embodiment, vitamin E in the form of d-alpha-tocopheryl acetate may be included in an amount of about 30 IU.

The compositions of the kits and methods of the present invention may comprise or use iron. A primary function of iron is to carry oxygen to bodily tissues via the hemoglobin part of red blood cells. Supplemental intake of iron is critical to preventing anemia, a disorder associated with a variety of physiological states including, for example, pregnancy. Bothwell, 72(Supp.) AM. J. CLIN. NUTR. 257S-64S (2000). Severe anemia may have adverse effects upon a mother and a fetus. Specifically, significant depression of hemoglobin has been associated with poor pregnancy outcome. Black, supra; Sifakis & Pharmakides, 900 ANN. N.Y. ACAD. SCI. 125-36 (2000). The kits and methods of the present invention may include iron in either chelated or nonchelated form. In a specific embodiment of the present invention, iron may be included in the form of polysaccharide iron complex. In another specific embodiment, iron may be included in the form of an equivalent molar amount of ferrous fumarate. For women in developed countries, however, who are generally clinically healthy and have access to adequate nutrition, the benefits of excessive iron supplementation are unclear, and there may be risks. B W Graves at al., J MIDWIFERY WOMENS HEALTH. 2001 May-June; 46(3):159-66 Thus, a "conservative" approach may be a lower supplementation of iron than currently available. Thus, in a specific embodiment of the present invention, iron may be included in amounts ranging from about 14 mg to about 44 mg. In another specific embodiment, iron may be included in amounts ranging from about 23 mg to about 35 mg. In another specific embodiment, iron may be included in amounts ranging from about 26 mg to about 32 mg. In another embodiment, iron may be included in an amount of about 29 mg.

In another specific embodiment, iron in the form of polysaccharide iron complex may be included in amounts ranging from about 14 mg to about 44 mg. In another specific embodiment, iron in the form of polysaccharide iron complex may be included in amounts ranging from about 23 mg to about 35 mg. In another specific embodiment, iron in the form of polysaccharide iron complex may be included in amounts ranging from about 26 mg to about 32 mg. In another embodiment, iron in the form of polysaccharide iron complex may be included in an amount of about 29 mg.

The compositions of the kits and methods of the present invention may comprise or use magnesium. Magnesium is found primarily in both bone and muscle and is important for over 300 different enzyme reactions. A primary function of magnesium is to bind to phosphate groups in adenosine triphosphate (ATP), thereby forming a complex that assists in the transfer of ATP phosphate. Magnesium also functions within cells as a membrane stabilizer. Magnesium plays roles in nucleic acid synthesis, glycolysis, transcription of DNA and RNA, amino acid activation, membrane transport, transketolase reactions, and protein synthesis. James L. L. Groff et al., ADVANCED NUTRITION AND HUMAN METABOLISM 341 (2d ed. 1996). It is also involved in the formation of cAMP, a cytosolic second messenger that plays a role in cell signaling mechanisms. Magnesium also functions both synergistically and antagonistically with calcium in neuromuscular transmission. RDA, supra at 188. Specifically, magnesium is critical for the maintenance of electrochemical potentials of nerve and muscle membranes and the neuromuscular junction transmissions, particularly important in the heart. Not surprisingly, magnesium deficiency is tied to cardiovascular disease and hypertension. Agus et al., 17 CRIT. CARE CLIN. 175-87 (2001). Indeed, oral magnesium therapy improves endothelial function in patients with coronary disease. Shechter et al., 102 CIRCULATION 2353-58 (2000).

Magnesium is available in a variety of salts and can be included in the kits and methods of the present invention in either chelated or nonchelated form. In one specific embodiment of the present invention, magnesium may be included in the form of magnesium oxide. In another specific embodiment, magnesium may be included in amounts ranging from about 12 mg to about 38 mg. In another specific embodiment, magnesium may be included in amounts ranging from about 20 mg to about 30 mg. In another specific embodiment, magnesium may be included in amounts ranging from about 22.5 mg to about 27.5 mg. In another embodiment, magnesium may be included in an amount of about 25 mg.

In another specific embodiment, magnesium in the form of magnesium oxide may be included in amounts ranging from about 12 mg to about 38 mg. In another specific embodiment, magnesium in the form of magnesium oxide may be included in amounts ranging from about 20 mg to about 30 mg. In another specific embodiment, magnesium in the form of magnesium oxide may be included in amounts ranging from about 22.5 mg to about 27.5 mg. In another embodiment, magnesium in the form of magnesium oxide may be included in an amount of about 25 mg.

The compositions of the kits and methods of the present invention may comprise or use zinc. Zinc plays a role in numerous metabolic activities such as nucleic acid production, protein synthesis, and development of the immune system. There are more than 200 zinc metalloenzymes including aldolase, alcohol dehydrogenase, RNA polymerase, and protein kinase C. Zima et al., 17 BLOOD PURIF. 182-86 (1999). Zinc stabilizes RNA and DNA structures, forms zinc fingers in nuclear receptors, and is a component of chromatin proteins involved in transcription and replication. Deficiencies of zinc during pregnancy have been shown to contribute to severe fetal abnormalities. Srinivas et al., 68(6) INDIAN J. PEDIATR. 519-22 (2001); Yang et al., 13(4) BIOMED. ENVIRON. SCI. 280-86 (2000); King, 71(Supp.) AM. J. CLIN. NUTR. 1334S-43S (2000). Indeed, the recommended daily allowance for zinc increases during pregnancy. A higher dose of zinc, however, is associated with causing nausea in some patients. Thus, for pregnant women or other patients that are more susceptible to nausea, a conservative amount of zinc that still provides adequate nutritional supplementation is desirable. In another specific embodiment, zinc may be included in amounts ranging from about 7 mg to about 23 mg. In another specific embodiment, zinc may be included in amounts ranging from about 12 mg to about 18 mg. In another specific embodiment, zinc may be included in amounts ranging from about 13.5 mg to about 16.5 mg. In another embodiment, zinc may be included in an amount of about 15 mg.

Zinc is available in many forms and may be included in the kits and methods of the present invention in chelated or nonchelated form. In a specific embodiment of the present invention, zinc may be included in the form of zinc oxide. In another specific embodiment, zinc in the form of zinc oxide may be included in amounts ranging from about 7 mg to about 23 mg. In another specific embodiment, zinc in the form of zinc oxide may be included in amounts ranging from about 12 mg to about 18 mg. In another specific embodiment, zinc in the form of zinc oxide may be included in amounts ranging from about 13.5 mg to about 16.5 mg. In another embodiment, zinc in the form of zinc oxide may be included in an amount of about 15 mg.

The compositions of the kits and methods of the present invention may comprise or use omega-3 fatty acids. Omega-3 fatty acids play integral roles in physiological mechanisms that serve to prevent, treat and/or alleviate the occurrence or negative effects of some diseases and has shown multiple health-promoting properties in adults. For example, omega-3 fatty acids are linked to health benefits such as preventing the occurrence of cancer, preventing the occurrence of heart disease, and are helpful in brain health and immune function. Indeed, omega-3 fatty acids include essential fatty acids linked to numerous health benefits, such as docahexaenoic acid (or docosahexaenoic acid, DHA), eicosapentaenoic acid (EPA) and α-linolenic acid (ALA). In another specific embodiment, the kits and methods of the present invention may comprise or use Docahexaenoic acid (or docosahexaenoic acid, DHA). In another specific embodiment, the kits and methods of the present invention may comprise or use eicosapentaenoic acid (EPA). In another specific embodiment, the kits and methods of the present invention may comprise or use a-linolenic acid (ALA).

The omega-3 fatty acid DHA, a major component of fish oil, has been shown to be of particular importance, especially during pregnancy or for lowering blood pressure. Indeed, studies suggest that DHA, but not EPA, reduce ambulatory blood pressure and heart rate in hyperlipidemic men. T A Mori et al., HYPERTENSION. 34:253-260 (1999). The results of this study thus suggest that DHA is the principal fatty acid in fish and fish oils that is responsible for blood pressure and heart rate effects in humans. Id.

Further, DHA is vital for optimal fetal and infant brain/cognitive development, as well as for normal brain function throughout life. F M Rioux, O. Hernell et al., ACTA PAEDIATR 95(2):137-144 (2006). The sleep patterns of infants born to mothers with higher plasma phospholipid DHA suggest greater central nerve system maturity. S R Cheruku, C J Lammi-Keefe et al., AM J CLIN NUTR 76:608-613, 2002. Additionally, children with Attention Deficit Hyperactivity Disorder (ADHD) have been shown to have abnormal levels of DHA. E A Mitchell, M. Manku et al., CLIN PEDIATR 26:406-411 (1986); L J Stevens, J R Burgess et al., PHYSIOL BEHAV 59:915-920 (1996). Studies have indicated a correlation between maternal DHA intake and intelligence quotient in the child. The direct correlation between brain development and systemic DHA status is secondary to the fact that DHA is taken up by the brain in preference to other fatty acids. Adequate DHA levels in pregnancy have also been correlated with optimizing the length of gestation and decreasing the risk of neurodevelopmental psychopathology. These critical findings have prompted the National Institute of Health (NIH) to recommend that pregnant women consume at least 300 mg of omega-3 fatty acids during pregnancy. N. Neurenger et al., NUTR REV 44:285-294 (1986); G. Hornstra et al., AM J CLIN NUTR 71:285 S-291S (2000); I B Helland et al., PEDIATRICS 111:E39-E44 (2003); F. Facchinetti et al., EUR REV MED PHARMACOL SCI 9(1):41-48 (2005); R K McNamara et al., PROSTAGLANDINS LEUKOT ESSENT FATTY ACIDS (29 Aug. 2006).

DHA is also important for the development of the infant retina and improving the visual acuity of the infant. C A Francois, W E Connor et al., AM J CLIN NUTR 77:226-233 (2003). Preterm infants have a more rapid development of visual acuity if fed human milk or formula enriched with DHA, compared to standard formula. M H Jorgensen, K F Michaelsen et al., LIPIDS 31(1):99-105 (1996). An increase in visual acuity has also been observed to develop more rapidly in term infants breast-fed from mothers whose diets are supplemented with DHA. Id.

In addition to the aforementioned benefit of DHA to the developing child, this essential fatty acid has also shown multiple health-promoting properties in adults. These include anti-thrombotic, anti-inflammatory and anti-atherosclerotic activity, all of which reduce the risk of heart disease. M Laidlaw and B J Holub, AM J CLIN NUTR 77:37-42 (2003). Inverse relationships have also been found between systemic levels of omega-3 fatty acids such as DHA and incidence and severity of mood disorders and depression, including post-partum depression. Therefore, introduction of omega-3 during pregnancy has a double benefit, to both child and mother. F B Hu et al., JAMA 287(14):1815-1821 (2002); C. Von Schacky et al., ANN INTERN MED 130:554-562 (1999); G. Parker et al., AM J PSYCHIATRY 163(6):969-978 (2006); S J Otto et al., PROSTAGLANDINS LEUKOT ESSENT FATTY ACIDS 69(3):237-243 (2003).

For women, DHA is particularly useful in counteracting the progression of breast cancer. Human breast cancer cells exposed to DHA exhibit an increase in cell death by apoptosis. B A Stoll, BR J NUTR 87(3):193-198, 2002. DHA also inhibits cyclooxygenase-2, which promotes mammary carcinogenesis. Id. DHA supplementation during pregnancy has also been shown to increase the length of gestation by about six days, helping mothers carry to a healthy full term. C M Smuts et al., OBSTETRICS AND GYNECOLOGY 101(3):469-479 (2003).

Intake of omega-3 fatty acids such as DHA not only leads to their incorporation into cell membrane lipids (B A Stoll, BR J NUTR 87(3):193-198 (2002)), but also storage in adipose tissue and secretion in breast milk. C A Francois, W E Connor et al., AM J CLIN NUTR 77:226-233 (2003). Although the human body can derive a limited amount of DHA from another fatty acid known as alpha-linolenic acid, this process is inefficient for optimal needs. A rich dietary source of direct DHA is fish. Id. However, some lactating women are vegetarians, have limited access to fish or simply do not like fish. A further problem with encouraging increased fish intake in pregnancy is that most species contain methyl mercury (MeHg) in various amounts. MeHg is a potent neurotoxin that can increase the risk of retarded cognitive development. This concern prompted both the United States Environmental Protection Agency (2004) and the Food and Drug Administration (2001) to issue advisories recommending that pregnant women modify their fish consumption. These recommendations have resulted in a reduced intake of fish during pregnancy, thus helping to protect against fetal MeHg related harm. However, this has concurrently reduced maternal intake of DHA. In fact, a recent dietary study of over 100 pregnant or nursing women in the United States showed an astonishingly low intake of DHA on average (60-80 mg/day), and a dangerously low percentage (<2) consumed the aforementioned recommended intake of 300 mg/day of DHA as set forth by the NIH. J T Cohen et al., AM J PREV MED, 29:353-365 (2005); U.S. Department of Health and Human Services, U.S. Environmental Protection Agency, "What you need to know about mercury in fish and shellfish," Report EPA-823-F-04-009 (March 2004); E. Oken et al., OBSTET GYNECOL 102:346-351 (2003).

In these cases, nutritional or prenatal supplements that include a dosage amount of DHA to meet the 300 mg/day recommendation is currently needed to provide the DHA necessary for physiological benefits. Thus, one embodiment of the present invention includes compositions of the kits and methods of the present invention designed to optimize health and wellness, minimize oxidative stress, and provide a beneficial increased supplementation of DHA to meet the 300 mg/day recommendation. In one embodiment of the present invention the omega-3 fatty acid such as DHA is provided in a separate dosage form from any other composition of the kits and methods of the present invention. Moreover, such a supplementation for, e.g., a pregnant woman or nursing mother, is a viable means of providing physiologically active DHA not only to the mother but also the infant.

DHA may be obtained in solid form, such as in a whole-cell microbial product, or in liquid form, such as in an oil. An example of DHA in oil form is DHASCO®-T vegetable oil from micro-algae (Martek Biosciences Corporation, Columbia, Md.). Modes of producing DHA, or food products or additives containing high concentrations of DHA, are known in the art. Some of these are described in U.S. Pat. Nos. 6,977,167; 5,407,957; 5,492,938; 5,340,594; 6,410,281; 6,451,567; 5,340,594; 6,607,900; 6,410,281; 6,451,567; and in U.S. Patent Application Publication Nos. 2003/0060509 A1; 2006/0099693 A1; 2005/0170479 A1; and 2006/0165735 A1, the disclosure of all of which are expressly incorporated by reference in their entireties.

In one embodiment, the compositions of the methods and kits of the present invention may include omega-3 fatty acids in amounts ranging from about 125 mg to about 375 mg. In another embodiment, the methods and kits of the present invention may include omega-3 fatty acids in amounts ranging from about 200 mg to about 300 mg. In yet another embodiment, the methods and kits of the present invention may include omega-3 fatty acids in amounts ranging from about 225 mg to about 275 mg. In a specific embodiment, the methods and kits of the present invention may include omega-3 fatty acids in an amount of about 250 mg.

In one embodiment, the methods and kits of the present invention may include DHA in amounts ranging from about 125 mg to about 375 mg. In another embodiment, the methods and kits of the present invention may include DHA in amounts ranging from about 200 mg to about 300 mg. In yet another embodiment, the methods and kits of the present invention may include DHA in amounts ranging from about 225 mg to about 275 mg. In a specific embodiment, the methods and kits of the present invention may include DHA in an amount of about 250 mg.

In another embodiment, the methods and kits of the present invention may include DHA derived from algae. DHA derived from algae, as opposed to being derived from fish oil, has numerous beneficial effects. First, the DHA from algae does not have the "fishy" smell that can come with DHA from fish oil. Indeed, high doses of DHA from fish oil may result in the patient having an unappealing after taste or a slight "fishy" body odor or "fishy" odor on the patient's breath. Second, DHA derived from algae can be more easily regulated to assure consistency and further remove the risk of added chemicals or other dangers. For example, DHA from algae would not have the risk of being tainted with mercury as opposed to DHA from fish oil. Thus, DHA from algae provides pregnant women and neonate with DHA without this risk and dangers of mercury.

Each of the active ingredient vitamins, minerals and fatty acids of the present invention is available from numerous commercial sources, and in several active forms or salts thereof, as known to those of ordinary skill in the art. Hence, the methods and kits of the present invention are not limited to comprising or using any particular form of the vitamin, mineral or fatty acid ingredient described herein. Each of the vitamins, minerals and fatty acids can be blended to form a single composition or can form multiple compositions, which may be co-administered.

The kits and methods of the present invention may comprise or use a combination of the included vitamins, nutrients and minerals just described, in either chelated or non-chelated form. For example, the kits and methods of the present invention may include vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc and omega-3 fatty acids.

In another embodiment, the kits and methods of the present invention may comprise a first composition comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and a second composition comprising omega-3 fatty acids.

In another embodiment, the first and second composition may be administered to a patient. In another embodiment, the first and second composition may be co-administered at the same time. In another embodiment, the first and second composition may be co-administered, wherein one composition is administered before the other composition, in either order. In another embodiment, the first and second composition may be administered to the patient orally.

In another embodiment, the kits and methods of the present invention may comprise swallowable compositions comprising vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; another embodiment of the present invention may comprise swallowable compositions comprising omega-3 fatty acids such as DHA enclosed within a gel-cap. Another specific embodiment of the present invention may comprise compositions comprising omega-3 fatty acids such as DHA in liquid or oil form, in a bottle.

In another embodiment, the kits and methods of the present invention may comprise a first composition consisting essentially of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and a second composition consisting essentially of omega-3 fatty acids.

In another embodiment, the kits and methods of the present invention may comprise a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium and zinc; and a second composition consisting of omega-3 fatty acids.

In another embodiment, the kits and methods of the present invention may comprise a first composition including about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; and about 7.0 mg to about 23 mg of zinc.

In another embodiment, the kits and methods of the present invention may comprise a second composition including about 125 mg to about 375 mg omega-3 fatty acids such as DHA.

In another embodiment, the kits and methods of the present invention may comprise a first composition including about 880 IU to about 1320 IU of vitamin A; about 480 IU to about 720 IU beta carotene; about 320 IU to about 480 IU of vitamin $D_3$; about 48 mg to about 72 mg of vitamin C; about 24 IU to about 36 IU of vitamin E; about 0.8 mg to about 1.2 mg of vitamin $B_9$; about 1.3 mg to about 1.9 mg of vitamin $B_1$; about 1.5 mg to about 2.2 mg of vitamin $B_2$; about 12 mg to about 18 mg of vitamin $B_3$; about 2 mg to about 3 mg of vitamin $B_6$; about 4.0 mcg to about 6.0 mcg of vitamin $B_{12}$; about 23 mg to about 35 mg of iron; about 20 mg to about 30 mg of magnesium; and about 12 mg to about 18 mg of zinc. In another embodiment, the kits and methods of the present invention may comprise a second composition including about 187.5 mg to about 312.5 mg omega-3 fatty acids such as DHA.

In another embodiment, the kits and methods of the present invention may comprise a first composition including about 990 IU to about 1210 IU of vitamin A; about 540 IU to about 660 IU beta carotene; about 360 IU to about 440 IU of vitamin $D_3$; about 54 mg to about 66 mg of vitamin C; about 27 IU to about 33 IU of vitamin E; about 0.9 mg to about 1.1 mg of vitamin $B_9$; about 1.5 mg to about 1.75 mg of vitamin $B_1$; about 1.6 mg to about 2.0 mg of vitamin $B_2$; about 13.5 mg to about 16.5 mg of vitamin $B_3$; about 2.3 mg to about 2.8 mg of vitamin $B_6$; about 4.5 mcg to about 5.5 mcg of vitamin $B_{12}$; about 26 mg to about 32 mg of iron; about 22.5 mg to about 27.5 mg of magnesium; and about 13.5 mg to about 16.5 mg of zinc. In another embodiment, the kits and methods of the present invention may comprise a second composition including about 225 mg to about 275 mg omega-3 fatty acids such as DHA.

In another embodiment, the kits and methods of the present invention may comprise a first composition including about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; and about 15 mg of zinc. In another embodiment, the kits and methods of the present invention may comprise a second composition including about 250 mg omega-3 fatty acids such as DHA.

In another specific embodiment, the kits and methods of the present invention may include specific forms of each ingredient. For example, the kits and methods of the present invention may include vitamin A in the form of acetate, beta carotene, vitamin $B_1$ in the form of thiamine mononitrate, vitamin $B_2$ in the form of riboflavin, vitamin $B_3$ in the form of niacinamide, vitamin $B_6$ in the form of pyridoxine hydrochloride, vitamin $B_9$ in the form of folic acid, vitamin $B_{12}$ in the form of cyanocobalamin, vitamin C in the form of ascorbic acid, vitamin $D_3$ in the form of cholecalciferol, vitamin E in the form of d-alpha-tocopheryl acetate, iron in the form of polysaccharide iron complex, magnesium in the form of magnesium oxide, zinc in the form of zinc oxide and omega-3 fatty acids in the form of DHA.

In another embodiment, the kits and methods of the present invention may comprise a first composition comprising vitamin A in the form of acetate, beta carotene, vitamin $B_1$ in the form of thiamine mononitrate, vitamin $B_2$ in the form of riboflavin, vitamin $B_3$ in the form of niacinamide, vitamin $B_6$ in the form of pyridoxine hydrochloride, vitamin $B_9$ in the form of folic acid, vitamin $B_{12}$ in the form of cyanocobalamin, vitamin C in the form of ascorbic acid, vitamin $D_3$ in the form of cholecalciferol, vitamin E, in the form of d-alpha-tocopheryl acetate, iron in the form of polysaccharide iron complex, magnesium in the form of magnesium oxide and zinc in the form of zinc oxide; and a second composition comprising omega-3 fatty acids in the form of DHA.

In another embodiment, the kits and methods of the present invention may comprise swallowable compositions comprising vitamin A in the form of acetate, beta carotene, vitamin $B_1$ in the form of thiamine mononitrate, vitamin $B_2$ in the form of riboflavin, vitamin $B_3$ in the form of niacinamide, vitamin $B_6$ in the form of pyridoxine hydrochloride, vitamin $B_9$ in the form of folic acid, vitamin $B_{12}$ in the form of cyanocobalamin, vitamin C in the form of ascorbic acid, vitamin $D_3$ in the form of cholecalciferol, vitamin E, in the form of d-alpha-tocopheryl acetate, iron in the form of polysaccharide iron complex, magnesium in the form of magnesium oxide and zinc in the form of zinc oxide; another embodiment of the present invention may comprise swallowable compositions comprising omega-3 fatty acids in the form of DHA enclosed within a gel-cap. Another specific embodiment of the present invention may comprise compositions comprising omega-3 fatty acids in the form of DHA in liquid or oil form, in a bottle.

In another specific embodiment, the swallowable compositions of the present invention may be in the form of gel-caps. Gel-caps consist of a filler comprising one or more pharmaceutically active materials dissolved or dispersed in an appropriate liquid vehicle encapsulated in a gelatin shell generally comprising gelatin together with a plasticizer such as glycerin or sorbitol. The filler material may comprise, for example, polyethylene glycols. Gel-caps are well known to those of ordinary skill in the art. See for example, U.S. Pat. Nos. 4,780,316; 5,419,916; 5,641,512; and 6,589,536. If more than one caplet or gel-cap is used, each individual caplet or gel-cap may be identical to the other caplets or gel-caps, or each may contain only some of the ingredients of the composition, so that the combination of the different caplets or gel-caps comprises a composition of the present invention. Another exemplary dosage of the compositions of the present invention may consist of one or more lozenges, the composition of each lozenge preferably being identical to each other lozenge. In another specific embodiment, the gel-cap may comprise sweeteners. In another specific embodiment, the gel-cap may comprise flavorants. In another specific embodiment, the flavorant may be orange flavor. In another specific embodiment, the gel-cap may comprise fillers. In another specific embodiment, the gel-cap may include active and/or inactive ingredients in a liquid or oil form.

In another embodiment, the kits and methods of the present invention may comprise a first composition consisting essentially of vitamin A in the form of acetate, beta carotene, vitamin $B_1$ in the form of thiamine mononitrate, vitamin $B_2$ in the form of riboflavin, vitamin $B_3$ in the form of niacinamide, vitamin $B_6$ in the form of pyridoxine hydrochloride, vitamin $B_9$ in the form of folic acid, vitamin $B_{12}$ in the form of cyanocobalamin, vitamin C in the form of ascorbic acid, vitamin $D_3$ in the form of cholecalciferol, vitamin E, in the form of d-alpha-tocopheryl acetate, iron in the form of polysaccharide iron complex, magnesium in the form of magnesium oxide, and zinc in the form of zinc oxide; and a second composition consisting essentially of omega-3 fatty acids in the form of DHA.

In another embodiment, the kits and methods of the present invention may comprise a first composition consisting of vitamin A in the form of acetate, beta carotene, vitamin $B_1$ in the form of thiamine mononitrate, vitamin $B_2$ in the form of riboflavin, vitamin $B_3$ in the form of niacinamide, vitamin $B_6$ in the form of pyridoxine hydrochloride, vitamin $B_9$ in the form of folic acid, vitamin $B_{12}$ in the form of cyanocobalamin, vitamin C in the form of ascorbic acid, vitamin $D_3$ in the form of cholecalciferol, vitamin E, in the form of d-alpha-tocopheryl acetate, iron in the form of polysaccharide iron complex, magnesium in the form of magnesium oxide, and zinc in the form of zinc oxide; and a second composition consisting of omega-3 fatty acids in the form of DHA.

In another embodiment, the kits and methods of the present invention may comprise a first composition including about 550 IU to about 1650 IU of acetate; about 300 IU to about 900 IU beta carotene; about 200 IU to about 600 IU of cholecalciferol; about 30 mg to about 90 mg of ascorbic acid; about 15 IU to about 45 IU of d-alpha-tocopheryl acetate; about 0.5 mg to about 1.5 mg of folic acid; about 1.0 mg to about 3.0 mg of thiamine mononitrate; about 1.0 mg to about 3.0 mg of riboflavin; about 7.0 mg to about 23 mg of niacinamide; about 1.0 mg to about 4.0 mg of pyridoxine hydrochloride; about 2.0 mcg to about 8.0 mcg of cyanocobalamin; about 14 mg to about 44 mg of polysaccharide iron complex; about 12 mg to about 38 mg of magnesium oxide; and about 7.0 mg to about 23 mg of zinc oxide.

In another embodiment, the kits and methods of the present invention may comprise a second composition including about 125 mg to about 375 mg of DHA.

In another embodiment, the kits and methods of the present invention may comprise a first composition including about 880 IU to about 1320 IU of acetate; about 480 IU to about 720 IU beta carotene; about 320 IU to about 480 IU of cholecalciferol; about 48 mg to about 72 mg of ascorbic acid; about 24 IU to about 36 IU of d-alpha-tocopheryl acetate; about 0.8 mg to about 1.2 mg of folic acid; about 1.3 mg to about 1.9 mg of thiamine mononitrate; about 1.5 mg to about 2.2 mg of riboflavin; about 12 mg to about 18 mg of niacinamide; about 2 mg to about 3 mg of pyridoxine hydrochloride; about 4.0 mcg to about 6.0 mcg of cyanocobalamin; about 23 mg to about 35 mg of polysaccharide iron complex; about 20 mg to about 30 mg of magnesium oxide; and about 12 mg to about 18 mg of zinc oxide. In another embodiment, the kits and methods of the present invention may comprise a second composition including about 200 mg to about 300 mg of DHA.

In another embodiment, the kits and methods of the present invention may comprise a first composition including about 990 IU to about 1210 IU of acetate; about 540 IU to about 660 IU beta carotene; about 360 IU to about 440 IU of cholecalciferol; about 54 mg to about 66 mg of ascorbic acid; about 27 IU to about 33 IU of d-alpha-tocopheryl acetate; about 0.9 mg to about 1.1 mg of folic acid; about 1.5 mg to about 1.75 mg of thiamine mononitrate; about 1.6 mg to about 2.0 mg of riboflavin; about 13.5 mg to about 16.5 mg of niacinamide; about 2.3 mg to about 2.8 mg of pyridoxine hydrochloride; about 4.5 mcg to about 5.5 mcg of cyanocobalamin; about 26 mg to about 32 mg of polysaccharide iron complex; about 22.5 mg to about 27.5 mg of magnesium oxide; and about 13.5 mg to about 16.5 mg of zinc oxide. In another embodiment, the kits and methods of the present invention may comprise a second composition including about 225 mg to about 275 mg of DHA.

In another embodiment, the kits and methods of the present invention may comprise a first composition including about 1100 IU of acetate; about 600 IU beta carotene; about 400 IU of cholecalciferol; about 60 mg of ascorbic acid; about 30 IU of d-alpha-tocopheryl acetate; about 1.0 mg of folic acid; about 1.6 mg of thiamine mononitrate; about 1.8 mg of riboflavin; about 15 mg of niacinamide; about 2.5 mg of pyridoxine hydrochloride; about 5.0 mcg of cyanocobalamin; about 29 mg of polysaccharide iron complex; about 25 mg of magnesium oxide; and about 15 mg of zinc oxide. In another embodiment, the kits and methods of the present invention may comprise a second composition including about 250 mg of DHA.

The active ingredients are available from numerous commercial sources, and in several active forms or salts thereof, known to those of ordinary skill in the art. Hence, the kits and methods of the present invention are not limited to comprising or using any particular form of the vitamin or mineral ingredient described herein.

B-complex vitamins, such as vitamin $B_6$ and $B_{12}$, vitamin $D_3$, and magnesium play integral roles in physiological mechanisms that serve to prevent, treat and/or alleviate the occurrence or negative effects of cardiovascular disease, colorectal cancer and osteoporosis. Supplementation with vitamins and minerals such as vitamin K may inhibit these beneficial effects. Thus, when creating or choosing a nutritional supplement, it is essential to understand the physiological needs and risks of individual patients and population groups and the interactions between various vitamins and minerals.

For example, vitamin K may have deleterious effects. Although vitamin K, or phylloquinone, plays a role in the process of maintaining bone health, it also plays a major role in the synthesis of coagulation factors. This delicate balance of coagulation is at times purposefully altered in those with, or at high risk of, cardiovascular disease. Increased intake of vitamin K can alter the efficacy of specific medications used for this purpose. Further, the human body produces vitamin K from naturally occurring intestinal bacteria, thus making deficiency of this nutrient rare. Due to these factors, broad spectrum vitamin K supplementation is discouraged. Kurnik et al., 37(11) ANN. PHARMACOTHER. 1603-06 (2003); Shearer, 345 LANCET 229-34 (1995). In a specific embodiment, the compositions of the kits and methods of the present invention may be substantially free of added vitamin K.

In another example, lactose is a disaccharide, or sugar that is found mainly in milk and dairy products. Lactose intolerance or the inability to properly digest and absorb this compound is relatively common. With this inability comes uncomfortable side effects such as abdominal bloating, pain, and diarrhea upon ingestion of lactose-containing foods. Since milk and dairy products are a primary source of both calcium and lactose, those who are lactose intolerant are more likely to have insufficient calcium intake and therefore osteoporosis. DiStefano et al., 122(7) GASTROENTEROL. 1793-99 (2002). In a specific embodiment, the compositions of the kits and methods of the present invention may be free of added lactose.

In another example, copper may be added in prenatal nutritional supplements to serve a role in protecting against disease and contributes to the overall health of the mother and developing child. Copper, however, may have adverse side effects outweighing any potential benefits. For example, high elevated serum levels of copper have been associated with post-partum depression. J W Crayton et al., J TRACE ELEM MED BIOL 21(1): 17-21 (2007). Thus, it is suggested that women who are pregnant or plan to become pregnant with a history of post-partum depression should carefully consider supplementation with copper. Id. Further, for this reason, copper may have deleterious effects on vitamins, antioxidants, nutrients or minerals of the present invention that are associated with reducing post-partum depression, such as DHA. In a specific embodiment, the compositions of the kits and methods of the present invention may be substantially free of added copper.

In another example, calcium may be added in prenatal nutritional supplements to serve a role in proper functioning of numerous intracellular and extracellular processes including, for example, muscle contraction, nerve conduction, blood coagulation, and of particular interest in the context of pregnancy and lactation and hormone release. Calcium, however, when added in high doses in nutritional supplements, can have undesirable side effects such as, constipation and other stomach problems such as nausea, vomiting and cramps. In a specific embodiment, the compositions of the kits and methods of the present invention may be substantially free of added calcium.

Manganese is a trace element essential for adequate growth and reproduction, bone development and carbohydrate metabolism. PRESENT KNOWLEDGE IN NUTRITION 7th Ed., pp. 334-339, E E Ziegler and L J Filer, Jr. eds., ILSI Press, Washington, D.C. (1996). As such, it is commonly included in nutritional supplements. Manganese toxicity, however, is also recognized as a serious health hazard to humans, when the mineral is taken in excess doses. Id. This toxicity may result in severe abnormalities of the central nervous system. Id. Manganese toxicity has been reported in an individual who consumed high amounts of manganese supplements over an extended period of time, and individuals who consumed water containing high manganese concentrations. Id. In a specific embodiment, the compositions of the methods and kits of the present invention may be substantially free of added manganese.

Thus, the kits and methods of the present invention provide a vitamin, mineral, and omega-3 fatty acid (such as DHA) supplementation that excludes ingredients that have deleterious effects on omega-3 fatty acids (such as DHA) or other undesirable side effects. Further, the kits and methods of the present invention provide a conservative or non-excessive amount of various ingredients to reduce the risk of undesirable side effects but still provide adequate nutritional supplementation for each ingredient. The kits and methods of the present invention may therefore be desirable for nutritional supplementation during periods such as prior to conception, throughout pregnancy, and during the postnatal period for lactating and non-lactating mother.

Specific patients, however, may also have unique or rare adverse reactions to antioxidants, vitamins or minerals added in the compositions of the present invention. Indeed, when choosing and administering a nutritional supplement, it is essential to understand the physiological needs and risks of individual patients and particular population groups, and the interactions between various vitamins and minerals. Thus, in particular instances, the compositions and methods of the present invention may also be substantially free of one or more of the added specific antioxidants, vitamins, nutrients or minerals in the compounds of the present invention to address such needs and risks.

In one specific embodiment, the kits and methods of the present invention may be substantially free of added vitamin A. In one embodiment, the compositions of the kits and methods of the present invention may be substantially free of added beta carotene. In one embodiment, the compositions of the kits and methods of the present invention may be substantially free of added vitamin $D_3$. In one embodiment, the compositions of the kits and methods of the present invention may be substantially free of added vitamin E. In one embodiment, the compositions of the kits and methods of the present invention may be substantially free of added vitamin $B_9$. In one embodiment, the compositions of the kits and methods of the present invention may be substantially free of added vitamin $B_1$. In one embodiment, the compositions of the kits and methods of the present invention may be substantially free of added vitamin $B_2$. In one embodiment, the compositions of the kits and methods of the present invention may be substantially free of added vitamin $B_6$. In one embodiment, the compositions of the kits and methods of the present invention may be substantially free of added vitamin $B_{12}$. In one embodiment, the compositions of the kits and methods of the present invention may be substantially free of added vitamin $B_3$.

In a specific embodiment of the present invention, other specific vitamins, nutrients and/or minerals may be excluded. For example, in a specific embodiment, the compositions of the kits and methods of the present invention may be substantially free of added alpha carotene; substantially free of added lutein; substantially free of added lycopene; substantially free of added zeaxanthin; substantially free of added vitamin $B_4$; substantially free of added vitamin $B_5$; substantially free of added vitamin $B_7$; substantially free of added vitamin $B_g$; substantially free of added vitamin $B_{10}$; substantially free of added vitamin $B_{11}$; substantially free of added calcium; substantially free of added chromium; substantially free of added copper; substantially free of added manganese; substantially free of added selenium; substantially free of added boron; substantially free of added odorless garlic; substantially free of added coenzyme Q-10; substantially free of added 1-carnitine; substantially free of added grape seed extract; substantially free of added green tea extract; substantially free of added quercetin; substantially free of added hawthorne berries; and/or substantially free of added alpha lipoic acid. In another embodiment of the present invention, the compositions are substantially free of other added vitamins and minerals.

In another specific embodiment, the compositions of the kits and methods of the present invention may be substantially free of one or more of added active compounds selected from the group consisting of lutein, lycopene, zeaxanthin, vitamin $B_4$, vitamin $B_5$, vitamin $B_7$, vitamin $B_g$, vitamin $B_{10}$, vitamin K, biotin, pantothenic acid, phosphorus, iodine, potassium, odorless garlic, coenzyme $Q_{10}$, l-carnitine, grape seed extract, chloride, sodium, green tea extract, quercetin, fluoride, hawthorne berries, and alpha lipoic acid.

In another specific embodiment, the compositions of the kits and methods of the present invention may be substantially free of one or more of added minerals and compounds selected from the group consisting of, copper, calcium, chromium, titanium, molybdenum, nickel, tin, silicon, vanadium, manganese, selenium, selenite, boron, bismuth, borax, bauxite, gold, silver, hydroxylapatite, mica, quartz, steatite, talc, sulfur, and zircon.

In another specific embodiment, the compositions of the kits and methods of the present invention may be substantially free of one or more of added inactive compounds selected from the group consisting of magnesium stearate, silica, silicon dioxide, magnesium silicate, dicalcium phosphate, povidone, titanium dioxide, sodium benzoate, alpha lipoic acid, lutein, lycopene, cellulose, croscarmellose sodium, stearic acid, cellulose, hydroxylpropyl cellulose, hydroxypropyl methylcellulose, titanium dioxide, polydextrose, triacetin, dicalcium phosphate, polyethylene glycol, polyvinylpyrrolidone, mineral oil, methocel, sodium lauryl sulfate, and talc.

A specific embodiment of the present invention may comprise swallowable compositions. Swallowable compositions are well known in the art and are those that do not readily dissolve when placed in the mouth and may be swallowed whole without any chewing or discomfort. In a specific embodiment of the present invention the swallowable compositions may have a shape containing no sharp edges and a smooth, uniform and substantially bubble free outer coating.

To prepare the swallowable compositions of the present invention, each of the active ingredients may be combined in intimate admixture with a suitable carrier according to conventional compounding techniques. In a specific embodiment of the swallowable compositions of the present invention, the surface of the compositions may be coated with a polymeric film. Such a film coating has several beneficial effects. First, it reduces the adhesion of the compositions to the inner surface of the mouth, thereby increasing the patient's ability to swallow the compositions. Second, the film may aid in masking the unpleasant taste of certain drugs. Third, the film coating may protect the compositions of the present invention from atmospheric degradation. Polymeric films that may be used in preparing the swallowable compositions of the present invention include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia. Pharmaceutical carriers and formulations for swallowable compounds are well known to those of ordinary skill in the art. See generally, e.g., WADE & WALLER, HANDBOOK OF PHARMACEUTICAL EXCIPIENTS ($2^{nd}$ ed. 1994).

In a specific embodiment of the present invention, the compositions may comprise chewable compositions. Chewable compositions are those that have a palatable taste and mouthfeel, are relatively soft and quickly break into smaller pieces and begin to dissolve after chewing such that they are swallowed substantially as a solution.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Chewable compositions preferably have a pleasant or palatable flavor. Palatable flavors may be achieved by including sweetening agents and/or flavorants. Sweetening agents that may be included in the compositions of the present invention include, by way of example and without limitation, sucrose, fructose, high fructose corn syrup, dextrose, saccharin sodium, maltodextrin, aspartame, potassium acesulfame, neohesperidin dihydrochalcone, sucralose, monoammonium glycyrrhizinate, and others known to those of ordinary skill in the art. As used herein, the term "flavorant" means natural or artificial compounds used to impart a pleasant flavor and often odor to a pharmaceutical preparation. Flavorants that may be used in the present invention include, for example and without limitation, natural and synthetic flavor oils, flavoring aromatics, extracts from plants, leaves, flowers, and fruits and combinations thereof. Such flavorants include, by way of example and without limitation, anise oil, cinnamon oil, vanilla, vanillin, cocoa, chocolate, natural chocolate flavor, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils, such as lemon, orange, lime and grapefruit oils; and fruit essences, including apple, pear, peach, berry, wildberry, date, blueberry, kiwi, strawberry, raspberry, cherry, plum, pineapple, and apricot. All of these flavorants are commercially available. In a specific embodiment of the present invention, flavorants that may be used include natural berry extracts and natural mixed berry flavor, as well as citric and malic acid. The amount of flavorants used may depend on a number of factors, including desired taste characteristics. While not necessary, one or more of these sweetening agents and/or flavorants also may be included in the swallowable compositions of the present invention. In a specific embodiment, the chewable compositions may have a natural berry flavor.

In addition to having a palatable flavor, chewable compositions also should have a pleasant mouthfeel. A variety of ingredients can be included in the compositions of the present invention to enhance mouthfeel.

In the chewable compositions of the present invention, sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Further, by way of example and without limitation, fondant or gums such as gelatin, agar, arabic gum, guar gum, and carrageenan may be added to improve the chewiness of the compositions. Fatty materials that may be included in the present invention include, by way of example and without limitation, vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used in the present invention to enhance the texture, the mouthfeel, or both of the chewable nutritional supplement compositions described herein. By "enhance the texture" it is meant that the alkyl polysiloxane improves one or more of the stiffness, the brittleness, and the chewiness of the chewable supplement, relative to the same preparation lacking the alkyl polysiloxane. By "enhance the mouthfeel" it is meant that the alkyl polysiloxane reduces the gritty texture of the supplement once it has liquefied in the mouth, relative to the same preparation lacking the alkyl polysiloxane.

Alkyl polysiloxanes generally comprise a silicon and oxygen-containing polymeric backbone with one or more alkyl groups pending from the silicon atoms of the back bone. Depending upon their grade, they can further comprise silica gel. Alkyl polysiloxanes are generally viscous oils. Exemplary alkyl polysiloxanes that can be used in the swallowable, chewable or dissolvable compositions of the present invention include, by way of example and without limitation, monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than about 90.5% by weight $(CH_3)_3$—Si{OSi$(CH_3)_2$}$CH_3$ in admixture with about 4.0% to about 7.0% by weight $SiO_2$.

To prevent the stickiness that can appear in conventional chewable compositions and to facilitate conversion of the active ingredients to emulsion or suspension upon taking, the compositions of the present invention, may further comprise emulsifiers such as, by way of example and without limitation, glycerin fatty acid ester, sorbitan monostearate, sucrose fatty acid ester, lecithin and mixtures thereof. In a specific embodiment, one or more of such emulsifiers may be present in an amount of about 0.01% to about 5.0%, by weight of the administered compositions. If the level of emulsifier is lower or higher than the said range, the emulsification cannot be realized, or wax value will rise.

Chewable compositions should begin to break and dissolve in the mouth shortly after chewing begins such that the compositions can be swallowed substantially as a solution. The dissolution profile of chewable compositions may be enhanced by including rapidly water-soluble fillers and excipients. Rapidly water-soluble fillers and excipients preferably dissolve within about 60 seconds of being wetted with saliva. Indeed, it is contemplated that if enough water-soluble excipients are included in the compositions of the present invention, they may become dissolvable rather than chewable composition forms. Examples of rapidly water soluble fillers suitable for use with the present invention include, by way of example and without limitation, saccharides, amino acids and the like. In a specific embodiment, the saccharide may be a mono-, di- or oligosaccharide. Examples of saccharides which may be added to the compositions of the present invention include, by way of example and without limitation, sorbitol, glucose, dextrose, fructose, maltose and xylitol (all monosaccharides); and sucrose, lactose, glucose, galactose and mannitol (all disaccharides). Other suitable saccharides are oligosaccharides. Examples of oligosaccharides are dextrates and maltodextrins. Other water soluble excipients that may be used with the present invention include, by way of example and without limitation, amino acids such as alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine.

Disintegrants also may be included in the compositions of the present invention in order to facilitate dissolution. Disentegrants, including permeabilising and wicking agents, are capable of drawing water or saliva up into the compositions which promotes dissolution from the inside as well as the outside of the compositions. Such disintegrants, permeabilising and/or wicking agents that may be used in the present invention include, by way of example and without limitation, starches, such as corn starch, potato starch, pre-gelatinized and modified starches thereof, cellulosic agents, such as Acdi-sol, montmorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropylmethylcellulose.

Finally, dissolution of the compositions may be facilitated by including relatively small particles sizes of the ingredients used.

In addition to those described above, any appropriate fillers and excipients may be utilized in preparing the swallowable, chewable and/or dissolvable compositions of the present invention so long as they are consistent with the objectives described herein. For example, binders are substances used to cause adhesion of powder particles in granulations. Such compounds appropriate for use in the present invention include, by way of example and without limitation, acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, polyethylene glycol and others known to those of ordinary skill in the art.

Diluents also may be included in the compositions of the present invention in order to enhance the granulation of the compositions. Diluents can include, by way of example and without limitation, microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycin, and their mixtures.

Lubricants are substances used in composition formulations that reduce friction during composition compression. Lubricants that may be used in the present invention include, by way of example and without limitation, stearic acid, calcium stearate, magnesium stearate, zinc stearate, talc, mineral and vegetable oils, benzoic acid, poly(ethylene glycol), glyceryl behenate, stearyl fumarate, and others known to those of ordinary skill in the art.

Glidants improve the flow of powder blends during manufacturing and minimize composition weight variation. Glidants that may be used in the present invention include, by way of example and without limitation, silicon dioxide, colloidal or fumed silica, magnesium stearate, calcium stearate, stearic acid, cornstarch, talc and others known to those of ordinary skill in the art.

Colorants also may be included in the nutritional supplement compositions of the present invention. As used herein, the term "colorant" includes compounds used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide, red and others known to those of ordinary skill in the art. Coloring agents also can include pigments, dyes, tints, titanium dioxide, natural coloring agents, such as grape skin extract, beet red powder, beta carotene, annato, carmine, turmeric, paprika and others known to those of ordinary skill in the art. It is recognized that no colorant is required in the nutritional supplement compositions described herein.

If desired, the compositions of the present invention may be sugar coated or enteric coated by standard techniques. The unit dose forms may be individually wrapped, packaged as multiple units on paper strips or in vials of any size, without limitation. The swallowable, chewable or dissolvable compositions of the present invention may be packaged in unit dose, rolls, bulk bottles, blister packs and combinations thereof, without limitation.

The swallowable, chewable or dissolvable compositions of the present invention may be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable nutritional supplements with improved mouthfeel. U.S. Pat. No. 5,965,162, relates to kits and methods for preparing multivitamin comestible units which disintegrate quickly in the mouth, especially when chewed. Further, all pharmaceutical carriers and formulations described herein are well known to those of ordinary skill in the art, and determination of workable proportions in any particular instance will generally be within the capability of the person skilled in the art. Details concerning any of the excipients of the invention may be found in WADE & WALLER, HANDBOOK OF PHARMACEUTICAL EXCIPIENTS (2nd ed. 1994). All active ingredients, fillers and excipients are commercially available from companies such as Aldrich Chemical Co., FMC Corp, Bayer, BASF, Alexi Fres, Witco, Mallinckrodt, Rhodia, ISP, and others.

A specific embodiment of the present invention may comprise swallowable compositions packaged in blister packs. Blister packs as packaging for swallowable compositions are well known to those of ordinary skill in the art. Blister packs may be made of a transparent plastic sheet which as been formed to carry a matrix of depression or blisters. One or more swallowable compositions are received in each depression or blister. A foil or plastic backing is then adhered across the plane of the sheet sealing the swallowable compositions in their respective blisters. Examples of materials used for the blister packs include, but are not limited to, aluminum, paper, polyester, PVC, and polypropylene. Alternative materials are known to those of ordinary skill in the art. To remove a swallowable composition, the depression material is pressed in and the composition is pushed through the backing material. Multiple blister packs may be placed in an outer package, often a box or carton for sale and distribution.

Another specific embodiment of the present invention may comprise swallowable compositions packaged in bottles. The bottle may be glass or plastic in form with a pop or screw top cap. Bottle packaging for compositions in swallowable form are well known to those of ordinary skill in the art.

Additionally, the unit dose forms may be individually wrapped, packaged as multiple units on paper strips or in vials of any size, without limitation. The swallowable, chewable or dissolvable compositions of the invention may be packaged in unit dose, rolls, bulk bottles, blister packs and combinations thereof, without limitation.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

EXAMPLES

Without further elaboration, it is believed that one skilled in the art, using the preceding description, can utilize the present invention to the fullest extent. The following examples are illustrative only, and not limiting of the remainder of the disclosure in any way whatsoever.

Example 1

A first composition of the following formulation is prepared in chewable form, including the appropriate excipients, by standard methods known to those of ordinary skill in the art:

| | |
|---|---|
| Vitamin A (acetate) | 1100 IU |
| Beta Carotene | 600 IU |
| Vitamin $B_1$ (thiamine mononitrate) | 1.6 mg |
| Vitamin $B_2$ (riboflavin) | 1.8 mg |
| Vitamin $B_3$ (niacinamide) | 15 mg |
| Vitamin $B_6$ (pyridoxine hydrochloride) | 2.5 mg |
| Vitamin $B_9$ (folic acid) | 1000 µg |
| Vitamin $B_{12}$ (cyanocobalamin) | 5 µg |
| Vitamin C (ascorbic acid) | 60 mg |
| Vitamin D (cholecalciferol) | 400 IU |
| Vitamin E (d-alpha-tocopheryl acetate) | 30 IU |
| Iron (polysaccharide complex) | 29 mg |
| Magnesium (magnesium oxide) | 25 mg |
| Zinc (zinc oxide) | 15 mg |

A second composition of the following formulation is prepared in gel-cap form by standard methods known to those of ordinary skill in the art:

| DHA, an omega-3 fatty acid | 250 mg |
|---|---|

Example 2

A study is undertaken to evaluate the effectiveness of the compositions of the present invention in the treatment of patients. The objective of the study is to determine whether oral intake of the compositions results in an improvement of the nutritional status of patients with regard to the specific vitamins and minerals contained in the administered compositions.

A double-blind, placebo controlled study is conducted over a six-month period. A total of 120 subjects (60 pregnant women entering the second trimester of pregnancy and 60 lactating women), aged 20-35 years, are chosen for the study. An initial assessment of the nutritional status of each woman is conducted. Vitamin A, beta carotene and vitamin $B_6$ are measured using high performance liquid chromatography. Erythrocyte transketolase activity is used to measure vitamin $B_1$ levels. Vitamin $B_2$ levels are determined by assessment of erythrocyte glutathione reductase activity. Vitamin $B_3$ levels are assessed by measuring urinary excretion of N'methylnicotinamide and its pyridone. Vitamin $B_9$ is measured by radioimmunoassay (RIA), specifically The Solid Phase No Biol Folic Acid Kit (Diagnostic Products, Los Angeles, Calif.). Vitamin $B_{12}$ is measured by RIA using human intrinsic factor as a binder. Vitamin C levels are measured by spectrophotometric and colorimetric methods. Vitamin D is measured using an extraction double-antibody RIA (Dia Sorin, Inc., Stillwater, Minn.). The peroxide hemolysis test is used to determine vitamin E status. Iron levels are measured using standard spectrophotometry. Similarly, magnesium levels are measured by absorbance of a magnesium chelate with xylidl blue at 660 nM. Zinc levels are assessed using flame atomic absorption spectrometry (Perkins Elmer 460, Norwalk, Conn.). DHA is measured and quantified using gas chromatography procedures.

Additionally, total serum homocysteine levels are determined by extraction on the Multi-Prep® gravity series GVSA-100 column, a strong anion exchange gravity flow column, and measurement by gas chromatography/mass spectrometry. Biochemical Diagnostics, Austin, Tex.

The 120 subjects are separated into four separate groups of 30 women. In a first group comprising only pregnant women and in a second group comprising only lactating women, each subject is administered one dosage form of the composition as described in Example 1 twice a day. In a third group comprising only pregnant women and in a fourth group comprising only lactating women, each subject is administered one placebo dosage form twice a day. Thus, dosage form administration occurs every 12 hours. No other nutritional supplements are taken by the subjects during the assessment period.

An assessment of the nutritional status of each woman is conducted utilizing the methods described above at one month intervals for a six month period. The data is evaluated using multiple linear regression analysis and a standard t-test. In each analysis, the baseline value of the outcome variable is included in the model as a covariant. Treatment by covariant interaction effects is tested by the method outlined by Weigel & Narvaez, 12 CONTROLLED CLINICAL TRIALS 378-94 (1991). If there are no significant interaction effects, the interaction terms are removed from the model. The regression model assumptions of normality and homogeneity of variance of residuals are evaluated by inspection of the plots of residuals versus predicted values. Detection of the temporal onset of effects is done sequentially by testing for the presence of significant treatment effects at 1, 2, 3, 4, 5, and 6 months, proceeding to the earlier time in sequence only when significant effects have been identified at each later time period. Changes from the baseline within each group are evaluated using paired t-tests. In addition, analysis of variance is performed on all baseline measurements and measurable subject characteristics to assess homogeneity between groups. All statistical procedures are conducted using the Statistical Analysis System (SAS Institute Inc., Cary, N.C.). An alpha level of 0.05 is used in all statistical tests.

A statistically significant improvement in the nutritional status of vitamin, mineral, and DHA levels measured is observed in the treated subjects over the controls upon completion of the study. Homocysteine levels in women receiving supplements remain unelevated. Therefore, the study confirms that oral administration of the compositions of the present invention is effective in improving the nutritional status of patients. The length of gestation is increased by approximately six days in women receiving supplements, due to DHA intake, and their homocysteine levels are not elevated, due to folic acid intake, leading to a better prognosis regarding risk of neural tube defects in their infants.

While specific embodiments of the present invention have been described, other and further modifications and changes may be made without departing from the spirit of the invention. All further and other modifications and changes are included that come within the scope of the invention as set forth in the claims. The disclosure of each publication cited above is expressly incorporated by reference in its entirety to the same extent as if each were incorporated by reference individually.

What is claimed is:

1. A method comprising co-administering a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc, and one or more pharmaceutically acceptable carriers to a patient and a second composition comprising omega-3 fatty acids to said patient, wherein said second composition is substantially free of added vitamins and minerals.

2. The method of claim 1, wherein said omega-3 fatty acids comprise docahexaenoic acid (DHA).

3. The method of claim 2, wherein said docahexaenoic acid is derived from algae.

4. The method of claim 1, wherein said first composition and said second composition are co-administered at the same time.

5. The method of claim 1, wherein said first composition and said second composition are co-administered to said patient, one said composition before the other said composition, in either order.

6. The method of claim 1, wherein said first composition is administered to said patient orally and said second composition is administered to said patient orally.

7. The method of claim 1, wherein one or both of said first and said second composition is in a swallowable form.

8. The method of claim 1, wherein one or both of said first and said second composition is in a chewable form.

9. The method of claim 1, wherein one or both of said first and said second composition is in a dissolvable form.

10. The method of claim 1, wherein said first composition is in a different form than said second composition.

11. The method of claim 1, wherein said second composition further comprises a pharmaceutically acceptable carrier.

12. The method of claim 11, wherein said pharmaceutically acceptable carriers are one or more selected from the group consisting of binders, diluents, lubricants, glidants, colorants, emulsifiers, disintegrants, starches, water, oils, alcohols, preservatives and sugars.

13. The method of claim 1, wherein said first composition further comprises a sweetening agent and said second composition further comprises a sweetening agent.

14. The method of claim 1, wherein said first composition further comprises a flavorant and said second composition further comprises a flavorant.

15. The method of claim 1, wherein said first composition consists of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc; and one or more pharmaceutically acceptable carriers.

16. The method of claim 1, wherein said first composition consists of about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; about 15 mg of zinc; and one or more pharmaceutically acceptable carriers.

17. The method of claim 1, wherein said omega-3 fatty acids are present in the amount of about 125 mg to about 375 mg.

18. The method of claim 1, wherein said omega-3 fatty acids are present in the amount of about 200 mg to about 300 mg.

19. The method of claim 1, wherein said omega-3 fatty acids are present in the amount of about 225 mg to about 275 mg.

20. The method of claim 1, wherein said omega-3 fatty acids are present in the amount of about 250 mg.

21. The method of claim 1, wherein said omega-3 fatty acids are enclosed within a gel-cap.

22. The method of claim 1, wherein said second composition is in liquid form.

23. A kit comprising: a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc, and one or more pharmaceutically acceptable carriers; and a second composition comprising omega-3 fatty acids; wherein said first and second compositions are packaged for co-administration to a patient, and wherein said second composition is substantially free of added vitamins and minerals.

24. The kit of claim 23, wherein said omega-3 fatty acids comprise docahexaenoic acid (DHA).

25. The kit of claim 24, wherein said docahexaenoic acid is derived from algae.

26. The kit of claim 23, wherein said first composition and said second composition are packaged for co-administration to said patient at the same time.

27. The kit of claim 23, wherein said first composition and said second composition are packaged for co-administration to said patient, wherein one said composition is administered before the other said composition, in either order.

28. The kit of claim 23, wherein said first composition and said second composition are packaged for administration to said patient orally.

29. The kit of claim 23, wherein one or both of said first and said second composition is in a swallowable form.

30. The kit of claim 23, wherein one or both of said first and said second composition is in a chewable form.

31. The kit of claim 23, wherein one or both of said first and said second composition is in a dissolvable form.

32. The kit of claim 23, wherein said first composition is in a different form than said second composition.

33. The kit of claim 23, wherein said omega-3 fatty acids are enclosed within a gel-cap.

34. The kit of claim 23, wherein said second composition is in liquid form.

35. The kit of claim 23, wherein said first composition consists of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc; and one or more pharmaceutically acceptable carriers.

36. The kit of claim 23, wherein said first composition consists of about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; about 15 mg of zinc; and one or more pharmaceutically acceptable carriers.

37. The kit of claim 23, wherein said omega-3 fatty acids are present in the amount of about 125 mg to about 375 mg.

38. The kit of claim 23, wherein said omega-3 fatty acids are present in the amount of about 200 mg to about 300 mg.

39. The kit of claim 23, wherein said omega-3 fatty acids are present in the amount of about 225 mg to about 275 mg.

40. The kit of claim 23, wherein said omega-3 fatty acids are present in the amount of about 250 mg.

41. The kit of claim 23, wherein said packaging is selected from the group consisting of bottles and blister packs.

42. The kit of claim 41, wherein said blister packs are sold together and said blister packs comprise a first blister pack containing said first composition and a second blister pack containing said second composition.

43. The kit of claim 41, wherein said blister pack contains both said first composition and said second composition paired together per unit dose.

44. The kit of claim 41, wherein said blister packs are sold separately and said blister packs comprise a first blister pack containing said first composition and a second blister pack containing said second composition.

45. The kit of claim 41, wherein said blister packs containing said first composition and said second composition are advertised as more effective if co-administered.

46. The kit of claim 45, wherein said advertisements are selected from one or more of the group consisting of internet, print, and product packaging advertisements.

47. A method comprising providing the kit of claim 23 to patients.

48. A method comprising co-administering a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc and one or more pharmaceutically acceptable carriers to a patient; and a second composition comprising DHA and one or more pharmaceutically acceptable carriers to said patient, wherein said second composition is substantially free of added vitamins and minerals.

49. The method of claim 48, wherein said first composition consists of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc and one or more pharmaceutically acceptable carriers; and said second composition comprises about 125 mg to about 375 mg of DHA and one or more pharmaceutically acceptable carriers.

50. The method of claim 48, wherein said first composition consists of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc and one or more pharmaceutically acceptable carriers; and said second composition comprises about 125 mg to about 375 mg of DHA and one or more pharmaceutically acceptable carriers.

51. A kit comprising: a first composition consisting of vitamin A, beta carotene, vitamin $B_1$, vitamin $B_2$, vitamin $B_3$, vitamin $B_6$, vitamin $B_9$, vitamin $B_{12}$, vitamin C, vitamin $D_3$, vitamin E, iron, magnesium, zinc and one or more pharmaceutically acceptable carriers; and a second composition comprising DHA and one or more pharmaceutically acceptable carriers; wherein said first and second compositions are packaged for administration to a patient, in any order, and wherein said second composition is substantially free of added vitamins and minerals.

52. The kit of claim 51, wherein said first composition consists of about 550 IU to about 1650 IU of vitamin A; about 300 IU to about 900 IU beta carotene; about 200 IU to about 600 IU of vitamin $D_3$; about 30 mg to about 90 mg of vitamin C; about 15 IU to about 45 IU of vitamin E; about 0.5 mg to about 1.5 mg of vitamin $B_9$; about 1.0 mg to about 3.0 mg of vitamin $B_1$; about 1.0 mg to about 3.0 mg of vitamin $B_2$; about 7.0 mg to about 23 mg of vitamin $B_3$; about 1.0 mg to about 4.0 mg of vitamin $B_6$; about 2.0 mcg to about 8.0 mcg of vitamin $B_{12}$; about 14 mg to about 44 mg of iron; about 12 mg to about 38 mg of magnesium; about 7.0 mg to about 23 mg of zinc and one or more pharmaceutically acceptable carriers; and said second composition comprises about 125 mg to about 375 mg of DHA and one or more pharmaceutically acceptable carriers.

53. The kit of claim 51, wherein said first composition consists of about 1100 IU of vitamin A; about 600 IU beta carotene; about 400 IU of vitamin $D_3$; about 60 mg of vitamin C; about 30 IU of vitamin E; about 1.0 mg of vitamin $B_9$; about 1.6 mg of vitamin $B_1$; about 1.8 mg of vitamin $B_2$; about 15 mg of vitamin $B_3$; about 2.5 mg of vitamin $B_6$; about 5.0 mcg of vitamin $B_{12}$; about 29 mg of iron; about 25 mg of magnesium; about 15 mg of zinc and one or more pharmaceutically acceptable carriers; and said second composition comprises about 250 mg of DHA and one or more pharmaceutically acceptable carriers.

54. A method comprising providing the kit of claim 51 to patients.

* * * * *